United States Patent [19]

Malfroy-Camine et al.

[11] Patent Number: 5,403,834
[45] Date of Patent: Apr. 4, 1995

[54] SYNTHETIC CATALYTIC FREE RADICAL SCAVENGERS USEFUL AS ANTIOXIDANTS FOR PREVENTION AND THERAPY OF DISEASE

[75] Inventors: Bernard Malfroy-Camine, Arlington, Mass.; Michel Baudry, Long Beach, Calif.

[73] Assignee: Eukarion, Inc., Arlington, Mass.

[21] Appl. No.: 987,474

[22] Filed: Dec. 7, 1992

[51] Int. Cl.$^6$ .............................................. A61K 31/555
[52] U.S. Cl. .................................................. 514/185
[58] Field of Search ......................................... 514/185

[56] References Cited

U.S. PATENT DOCUMENTS 5,106,841  4/1992  Scheer ................................. 514/185
5,223,538  6/1993  Fridovich et al. ................... 514/616

OTHER PUBLICATIONS

Foye, "Radio Protective Drugs" in Burger's *Medicinal Chemistry* 4th Ed., Wolf ed. pp. 11, 22, 29–35, 39, 44 (1981).
Sittig *Handbook of Toxic and Hazardous Chemicals and Carcinogens*, pp. 559–562, 639–641, 243–248, (1985).
Czapski and Goldstein (1990), "Superoxide Scavengers and Sod or Sod Mimics," in Antioxidants in Therapy and Preventive Medicine, Eds. Emerit et al., Plenum Press, New York, pp. 45–50.
de Garavilla et al. (1992), "Novel Low–Molecular–Weight Superoxide Dismutase Mimic Deferoxamine-Manganese Improves Survival Following Hemorrhagic and Endotoxic Shock," Drug Development Research 25:139–148.
Fu et al. (1991), "Mechanistic Study of a Synthetically Useful Model Using the Hypersensitive Probe trans-2–Phenyl-1-vinylcyclopropane," J. Organic Chem. 56:6497–6500.
Jacobsen et al. (1991), "Electronic Tuning of Asymmetric Catalysts," J. Organic Chem. 113:6703–6704.
Jacobsen et al. (1991), "Highly Enantioselective Epoxidation Catalysts Derived from 1,2-Diaminocyclohexane," J. Am. Chem. Soc. 113:7063–7064.
Lee and Jacobsen (1991), "Enantioselective Epoxidation of Conjugated Dienes and Enynes. Trans-Epoxides from Cis-Olefins," Tetra. Letts. 32:6533–6536.
Lee et al. (1991), "Enantiomerically Pure Epoxychromans via Asymmetric Catalysis," Tetra. Letts. 32:5055–5058.
Yamamoto et al. (1990), "Anti-tumor Promoting Action of Phthalic Acid Mono-n-butyl Ester Cupric Salt, A Biomimetic Superoxide Dismutase," Carcinogenesis 11:749–754.
Zhang and Jacobsen (1991), "Asymmetric Olefin Epoxidation with Sodium Hypochlorite Catalyzed by Easily Prepared Chiral Mn(III) Salen Complexes," J. Organic Chem. 56:2296–2298.
Zhang et al. (1990), "Enantioselective Epoxidation of Unfunctionalized Olefins Catalyzed by (Salen) manganese Complexes," J. Am. Chem. Sco. 112:2801–2803.
Coleman et al. (1981), "Characterization and Electrochemistry of Manganese(III) Complexes Containing Pentadentate Ligands," Inorg. Chem. 20:1253–1258.
Kensler et al. (1983), "Inhibition of Tumor Promotion by a Biomimetic Superoxide Dismutase," Science 75–77.
Kessel et al. (1980), "Iron(III), Manganese(III), and Cobalt(III) Complexes with Single Chelating o–Semiquinone Ligands," Inorg. Chem. 19:1170–1178.
Matsushita et al. (1981), "The Preparation and Characterization of Dichloromanganese(IV) Schiff Base Complexes," Bull. Chem. Soc. Jpn. 54:2646–2651.
Nagano et al. (1989), "Superoxide Dismutase Mimics Based On Iron In Vito," J. Biol. Chem. 264:9243–9249.

(List continued on next page.)

Primary Examiner—Raymond Henley, III
Assistant Examiner—T. J. Criares
Attorney, Agent, or Firm—Tracy J. Dunn

[57] ABSTRACT

The invention provides antioxidant salen-metal complexes in a form suitable for pharmaceutical administration to treat or prevent a disease associated with cell or tissue damage produced by free radicals such as superoxide.

6 Claims, 6 Drawing Sheets

OTHER PUBLICATIONS

Pasini et al. (1977), "Optically Active Complexes of Schiff Bases. Part 4. An Analysis of the Circular-dichroism Spectra of Some Complexes of Different Co-ordination Numbers with Quadridentate Schiff Bases of Optically Active Diamines," J. C. S. Dalton 346–356.

Jacobsen (1991), National Institute of General Medical Sciences Notice of Grant Award, Grant Number: 1 R01 GM 43214–01A1, Title: Chiral Complexes Designed to Catalyze Organic Reactions.

Jacobsen (1990), National Science Foundation, Presidential Young Investigator Award, Grant Number CHE-9057740.

SYNTHETIC CATALYTIC FREE RADICAL SCAVENGERS USEFUL AS ANTIOXIDANTS FOR PREVENTION AND THERAPY OF DISEASE

FIELD OF THE INVENTION

The invention provides pharmaceutical compositions of synthetic catalytic small molecule antioxidants and free radical scavengers for therapy and prophylaxis of disease, methods for using the small molecule antioxidants in prevention and treatment of pathological conditions, methods for using the small molecule antioxidants for targeted protection of tissues and/or cell types during cancer chemotherapy, and methods for using the small molecule antioxidants to prevent toxicologic damage to individuals exposed to irritating oxidants or other sources of oxidative damage, particularly oxygen-derived oxidative species such as superoxide radical. The compositions and methods of the invention are also used for preventing oxidative damage in human transplant organs and for inhibiting reoxygenation injury following reperfusion of ischemic tissues. The compositions and methods of the invention are also useful for chemoprevention of chemical carcinogenesis and alteration of drug metabolism involving epoxide or free oxygen radical intermediates.

BACKGROUND OF THE INVENTION

Molecular oxygen is an essential nutrient for non-facultative aerobic organisms, including, of course, humans. Oxygen is used in many important ways, namely, as the terminal electronic acceptor in oxidative phosphorylation, in many dioxygenase reactions, including the synthesis of prostaglandins and of vitamin A from carotenoids, in a host of hydroxylase reactions, including the formation and modification of steroid hormones, and in both the activation and the inactivation of xenobiotics, including carcinogens. The extensive P-450 system uses molecular oxygen in a host of important cellular reactions. In a similar vein, nature employs free radicals in a large variety of enzymic reactions.

Excessive concentrations of various forms of oxygen and of free radicals can have serious adverse effects on living systems, including the peroxidation of membrane lipids, the hydroxylation of nucleic acid bases, and the oxidation of sulfhydryl groups and of other sensitive moieties in proteins. If uncontrolled, mutations and cellular death result.

Biological antioxidants include well-defined enzymes, such as superoxide dismutase, catalase, selenium glutathione peroxidase, and phospholipid hydroperoxide glutathione peroxidase. Nonenzymatic biological antioxidants include tocopherols and tocotrienols, carotenoids, quinones, bilirubin, ascorbic acid, uric acid, and metal-binding proteins. Various antioxidants, being both lipid and water soluble, are found in all parts of cells and tissues, although each specific antioxidant often shows a characteristic distribution pattern. The so-called ovothiols, which are mercaptohistidine derivatives, also decompose peroxides nonenzymatically.

Free radicals, particularly free radicals derived from molecular oxygen, are believed to play a fundamental role in a wide variety of biological phenomena. In fact, it has been suggested that much of what is considered critical illness may involve oxygen radical ("oxyradical") pathophysiology (Zimmermen J. J. (1991) Chest 100: 189S). Oxyradical injury has been implicated in the pathogenesis of pulmonary oxygen toxicity, adult respiratory distress syndrome (ARDS), bronchopulmonary dysplasia, sepsis syndrome, and a variety of ischemia-reperfusion syndromes, including myocardial infarction, stroke, cardiopulmonary bypass, organ transplantation, necrotizing enterocolitis, acute renal tubular necrosis, and other disease. Oxyradicals can react with proteins, nucleic acids, lipids, and other biological macromolecules producing damage to cells and tissues, particularly in the critically ill patient.

Free radicals are atoms, ions, or molecules that contain an unpaired electron (Pryor, W. A. (1976) Free Radicals in Biol. 1: 1). Free radicals are usually unstable and exhibit short half-lives. Elemental oxygen is highly electronegative and readily accepts single electron transfers from cytochromes and other reduced cellular components; a portion of the $O_2$ consumed by cells engaged in aerobic respiration is univalently reduced to superoxide radical ($.O_2^-$) (Cadenas E. (1989) Ann. Rev. Biochem. 58: 79). Sequential univalent reduction of $.O_2^-$ produces hydrogen peroxide ($H_2O_2$), hydroxyl radical (.OH), and water.

Free radicals can originate from many sources, including aerobic respiration, cytochrome P-450-catalyzed monooxygenation reactions of drugs and xenobiotics (e.g., trichloromethyl radicals, $CCl_3.$, formed from oxidation of carbon tetrachloride), and ionizing radiation. For example, when tissues are exposed to gamma radiation, most of the energy deposited in the cells is absorbed by water and results in scission of the oxygen-hydrogen covalent bonds in water, leaving a single electron on hydrogen and one on oxygen creating two radicals H. and .OH. The hydroxyl radical, .OH, is the most reactive radical known in chemistry. It reacts with biomolecules and sets off chain reactions and can interact with the purine or pyrimidine bases of nucleic acids. Indeed, radiation-induced carcinogenesis may be initiated by free radical damage (Breimer L. H. (1988) Brit. J. Cancer 57: 6). Also for example, the "oxidative burst" of activated neutrophils produces abundant superoxide radical, which is believed to be an essential factor in producing the cytotoxic effect of activated neutrophils. Reperfusion of ischemic tissues also produces large concentrations of oxyradicals, typically superoxide (Gutteridge J. M. C. and Halliwell B. (1990) Arch. Biochem. Biophys. 283: 223). Moreover, superoxide may be produced physiologically by endothelial cells for reaction with nitric oxide, a physiological regulator, forming peroxynitrite, $ONOO^-$ which may decay and give rise to hydroxyl radical, .OH (Marletta, M. A. (1989) Trends Biochem. Sci. 14: 488; Moncada et al. (1989) Biochem. Pharmacol. 38: 1709; Saran et al. (1990) Free Rad. Res. Commun. 10: 221; Beckman et al. (1990) Proc. Natl. Acad. Sci. (U.S.A.) 87: 1620). Additional sources of oxyradicals are "leakage" of electrons from disrupted mitochondrial or endoplasmic reticular electron transport chains, prostaglandin synthesis, oxidation of catecholamines, and platelet activation.

Many free radical reactions are highly damaging to cellular components; they crosslink proteins, mutagenize DNA, and peroxidize lipids. Once formed, free radicals can interact to produce other free radicals and non-radical oxidants such as singlet oxygen ($^1O_2$) and peroxides. Degradation of some of the products of free radical reactions can also generate potentially damaging chemical species. For example, malondialdehyde is a reaction product of peroxidized lipids that reacts with virtually any amine-containing molecule. Oxygen free radicals also cause oxidative modification of proteins (Stadtman E. R. (1992) *Science* 257: 1220).

Aerobic cells generally contain a number of defenses against the deleterious effects of oxyradicals and their reaction products. Superoxide dismutases (SODs) catalyze the reaction:

$$2.O_2^- + 2H^+ \rightarrow O_2 + H_2O_2$$

which removes superoxide and forms hydrogen peroxide. $H_2O_2$ is not a radical, but it is toxic to cells; it is removed by the enzymatic activities of catalase and glutathione peroxidase (GSH-Px). Catalase catalyzes the reaction:

$$2H_2O_2 \rightarrow 2H_2O + O_2$$

and GSH-Px removes hydrogen peroxide by using it to oxidize reduced glutathione (GSH) into oxidized glutathione (GSSG) according to the following reaction:

$$2\,GSH + H_2O_2 \rightarrow GSSG + 2H_2O$$

Other enzymes, such as phospholipid hydroperoxide glutathione peroxidase (PLOOH-GSH-Px), converts reactive phospholipid hydroperoxides, free fatty acid hydroperoxides, and cholesterol hydroperoxides to corresponding harmless fatty acid alcohols. Glutathione S-transferases also participate in detoxifying organic peroxides. In the absence of these enzymes and in presence of transition metals, such as iron or copper, superoxide and hydrogen peroxide can participate in the following reactions which generate the extremely reactive hydroxyl radical $.OH^-$:

$$.O_2^- + Fe^{3+} \rightarrow O_2 + Fe^{2+}$$

$$H_2O_2 + Fe^{2+} \rightarrow .OH + OH^- + Fe^{3+}$$

In addition to enzymatic detoxification of free radicals and oxidant species, a variety of low molecular weight antioxidants such as glutathione, ascorbate, tocopherol, ubiquinone, bilirubin, and uric acid serve as naturally-occurring physiological antioxidants (Krinsky N. I. (1992) *Proc. Soc. Exp. Biol. Med.* 200:248–54). Carotenoids are another class of small molecule antioxidants and have been implicated as protective agents against oxidative stress and chronic diseases. Canfield et al. (1992) *Proc. Soc. Exp. Biol. Med.* 200:260 summarize reported relationships between carotenoids and various chronic diseases, including coronary heart disease, cataract, and cancer. Carotenoids dramatically reduce the incidence of certain premalignant conditions, such as leukoplakia, in some patients.

In an effort to prevent the damaging effects of oxyradical formation during reoxygenation of ischemic tissues, a variety of antioxidants have been used.

One strategy for preventing oxyradical-induced damage is to inhibit the formation of oxyradicals such as superoxide. Iron ion chelators, such as desferrioxamine (also called deferoxamine or Desferol) and others, inhibit iron ion-dependent .OH generation and thus act as inhibitors of free radical formation (Gutteridge et al. (1979) *Biochem. J.* 184: 469; Halliwell B. (1989) *Free Radical Biol. Med.* 645; Van der Kraaij et al. (1989) *Circulation* 80: 158). Amino-steroid-based antioxidants such as the 21-aminosteroids termed "lazaroids" (e.g., U74006F) have also been proposed as inhibitors of oxyradical formation. Desferrioxamine, allopurinol, and other pyrazolopyrimidines such as oxypurinol, have also been tested for preventing oxyradical formation in a myocardial stunning model system (Bolli et al. (1989) *Circ. Res.* 65: 607) and following hemorrhagic and endotoxic shock (DeGaravilla et al. (1992) *Drug Devel. Res.* 25: 139). However, each of these compounds has notable drawbacks for therapeutic usage. For example, deferoxamine is not an ideal iron chelator and its cellular penetration is quite limited.

Another strategy for preventing oxyradical-induced damage is to catalytically remove oxyradicals such as superoxide once they have been formed. Superoxide dismutase and catalase have been extensively explored, with some success, as protective agents when added to reperfusates in many types of experiments or when added pre-ischemia (reviewed in Gutteridge J. M. C. and Halliwell B. (1990) op.cit.). The availability of recombinant superoxide dismutase has allowed more extensive evaluation of the effect of administering SOD in the treatment or prevention of various medical conditions including reperfusion injury of the brain and spinal cord (Uyama et al. (1990) *Free Radic. Biol. Med.* 265; Lim et al. (1986) *Ann. Thorac. Surg.* 42: 282), endotoxemia (Schneider et al. (1990) *Circ. Shock* 30: 97; Schneider et al. (1989) *Prog. Clin. Biol. Res.* 308: 913, and myocardial infarction (Patel et al. (1990) *Am. J. Physiol.* 258: H369; Mehta et al. (1989) *Am. J. Physiol.* 257: H1240; Nejima et al. (1989) *Circulation* 79: 143; Fincke et al. (1988) *Arzneimittelforschung* 38: 138; Ambrosio et al. (1987) *Circulation* 75: 282), and for osteoarthritis and intestinal ischemia (Vohra et al. (1989) *J. Pediatr. Surg.* 24: 893; Flohe L. (1988) *Mol. Cell. Biochem.* 84: 123). Superoxide dismutase also has been reported to have positive effects in treating systemic lupus erythematosus, Crohn's disease, gastric ulcers, oxygen toxicity, burned patients, renal failure attendant to transplantation, and herpes simplex infection.

An alternative strategy for preventing oxyradical-induced damage is to scavenge oxyradicals such as superoxide once these have been formed, typically by employing small molecule scavengers which act stoichiometrically rather than catalytically. Congeners of glutathione have been used in various animal models to attenuate oxyradical injury. For example, N-2-mercaptopropionylglycine has been found to confer protective effects in a canine model of myocardial ischemia and reperfusion (Mitsos et al. (1986) *Circulation* 73: 1077) and N-acetylcysteine ("Mucomyst") has been used to treat endotoxin toxicity in sheep (Bernard et al. (1984) *J. Clin. Invest.* 73: 1772). Dimethyl thiourea (DMTU) and butyl-α-ephenylnitrone (BPN) are believed to scavenge the hydroxyl radical, .OH, and has been shown to reduce ischemia-reperfusion injury in rat myocardium and in rabbits (Vander Heide et al. (1987) *J. Mol. Cell. Cardiol.* 19: 615; Kennedy et al. (1987) *J. Appl. Physiol.* 63: 2426). Mannitol has also been used as a free radical scavenger to reduce organ injury during reoxygenation (Fox R. B. (1984) *J. Clin. Invest.* 74: 1456; Ouriel et al. (1985) *Circulation* 72: 254).

Thus, application of inhibitors of oxyradical formation and/or enzymes that remove superoxide and hydrogen peroxide and/or small molecule oxyradical scavengers have all shown promise for preventing reoxygenation damage present in a variety of ischemic pathological states and for treating or preventing various disease states associated with free radicals. However, each of these categories contains several drawbacks. For example, inhibitors of oxyradical formation typically chelate transition metals which are used in essential enzymatic processes in normal physiology and respiration; moreover, even at very high doses, these inhibitors do not completely prevent oxyradical formation. Superoxide dismutases and catalase are large polypeptides which are expensive to manufacture, do not penetrate cells or the blood-brain barrier, and generally require parenteral routes of administration. Free radical scavengers act stoichiometrically and are thus easily depleted and must be administered in high dosages to be effective.

Based on the foregoing, it is clear that a need exists for antioxidant agents which are efficient at removing dangerous oxyradicals, particularly superoxide and hydrogen peroxide, and which are inexpensive to manufacture, stable, and possess advantageous pharmacokinetic properties, such as the ability to cross the blood-brain barrier and penetrate tissues. Such versatile antioxidants would find use as pharmaceuticals, chemoprotectants, and possibly as dietary supplements. It is one object of the invention to provide a class of novel antioxidants which possess advantageous pharmacologic properties and which catalytically and/or stoichiometrically remove superoxide and/or hydrogen peroxide.

The references discussed herein are provided solely for their disclosure prior to the filing date of the present application. Nothing herein is to be construed as an admission that the inventors are not entitled to antedate such disclosure by virtue of prior invention. All publications cited are incorporated herein by reference.

SUMMARY OF THE INVENTION

In accordance with the foregoing objects, in one aspect of the invention pharmaceutical compositions are provided which have potent antioxidant and/or free radical scavenging properties and function as in vivo antioxidants. The pharmaceutical compositions of the invention comprise an efficacious dosage of at least one species of salen-transition metal complex, typically a salen-manganese complex such as a salen-Mn(III) complex. In one embodiment, the pharmaceutical composition comprises a salen-Mn complex which is a chelate of Mn(III) with a diamine derivative, such as ethylenediamine linked to two substituted salicylaldehydes. These pharmaceutical compositions possess the activity of dismutating superoxide (i.e., superoxide dismutase activity) and, advantageously, also converting hydrogen peroxide to water (i.e., catalase activity). The pharmaceutical compositions are effective at reducing pathological damage related to formation of oxyradicals such as superoxide and peroxides and other free radical species.

The invention also provides methods for treating and preventing pathological conditions by applying or administering compositions of salen-transition metal complexes in a therapeutic or prophylactic dosage. Salen-transition metal complexes used in the methods of the invention are typically salen-manganese complexes, such as Mn(III)-salen complexes. The invention provides methods for preventing or reducing ischemic/-reperfusion damage to critical tissues such as the myocardium and central nervous system. The invention also provides methods for preventing or reducing cellular damage resulting from exposure to various chemical compounds which produce potentially damaging free radical species, comprising administering a therapeutically or prophylactically efficacious dosage of at least one species of salen-transition metal complex, preferably a salen-manganese complex having detectable SOD activity and preferably also having detectable catalase activity. The antioxidant salen-transition metal complexes of the invention are administered by a variety of routes, including parenterally, topically, and orally.

In one aspect of the invention, a therapeutic or prophylactic dosage of a salen-transition metal complex of the present invention is administered alone or combined with (1) one or more antioxidant enzymes, such as a Mn-SOD, a Cu,Zn-SOD, or catalase, and/or (2) one or more free radical scavengers, such as tocopherol, ascorbate, glutathione, DMTU, N-acetylcysteine, or N-2-mercaptopropionylglycine and/or (3) one or more oxyradical inhibitors, such as desferrioxamine or allopurinol, and/or one or more biological modifier agents, such as calpain inhibitors. The formulations of these compositions is dependent upon the specific pathological condition sought to be treated or prevented, the route and form of administration, and the age, sex, and condition of the patient. These compositions are administered for various indications, including: (1) for preventing ischemic/reoxygenation injury in a patient, (2) for preserving organs for transplant in an anoxic, hypoxic, or hyperoxic state prior to transplant, (3) for protecting normal tissues from free radical-induced damage consequent to exposure to ionizing radiation and/or chemotherapy, as with bleomycin, (4) for protecting cells and tissues from free radical-induced injury consequent to exposure to xenobiotic compounds which form free radicals, either directly or as a consequence of monooxygenation through the cytochrome P-450 system, (5) for enhancing cryopreservation of cells, tissues, organs, and organisms by increasing viability of recovered specimens, and (6) for prophylactic administration to prevent: carcinogenesis, cellular senescence, cataract formation, formation of malondialdehyde adducts, HIV pathology and macromolecular crosslinking, such as collagen crosslinking.

In one aspect of the invention, salen-transition metal complexes are formulated for administration by the oral route by forming a pharmaceutical dosage form comprising an excipient and not less than 1 $\mu$g nor more than about 10 grams of at least one antioxidant salen-transition metal complex of the invention. Dietary formulations are administered for therapy of free radical-induced diseases and/or for the chemoprevention of neoplasia and/or oxidative damage associated with normal aerobic metabolism.

In another aspect of the invention, buffered aqueous solutions comprising at least one antioxidant salen-transition metal complex of the invention at a concentration of at least 1 nM but not more than about 100 mM is formulated for administration, usually at a concentration of about 0.1 to 10 mM, typically by intravenous route, to a patient undergoing or expected to undergo: (1) an ischemic episode, such as a myocardial infarction, cerebral ischemic event, transplantation operation, open heart surgery, elective angioplasty, coronary artery bypass surgery, brain surgery, renal infarction, traumatic hemorrhage, tourniquet application, (2) antineoplastic or antihelminthic chemotherapy employing a chemotherapeutic agent which generates free radicals, (3) endotoxic shock or sepsis, (4) exposure to ionizing radiation, (5) exposure to exogenous chemical compounds which are free radicals or produce free radicals, (6) thermal or chemical burns or ulcerations, or (7) hyperbaric oxygen. The buffered aqueous solutions of the invention may also be used, typically in conjunction with other established methods, for organ culture, cell culture, transplant organ maintenance, and myocardial irrigation. Nonaqueous formulations, such as lipid-based formulations are also provided, including stabilized emulsions. The antioxidant salen-metal compositions are administered by various routes, including intravenous injection, intramuscular injection, subdermal injection, intrapericardial injection, surgical irrigation, topical application, ophthalmologic application, lavage, gavage, enema, intraperitoneal infusion, mist inhalation, oral rinse, and other routes, depending upon the specific medical or veterinary use intended.

In another aspect of the invention, antioxidant salen-transition metal complexes of the invention are employed to modulate the expression of naturally-occurring genes or other polynucleotide sequences under the transcriptional control of an oxidative stress response element (e.g., an antioxidant responsive element, ARE), such as an antioxidant response element of a glutathione S-transferase gene or a NAD(P)H:quinone reductase gene. The antioxidant salen-metal complexes may be used to modulate the transcription of ARE-regulated polynucleotide sequences in cell cultures (e.g., ES cells) and in intact animals, particularly in transgenic animals wherein a transgene comprises one or more AREs as transcriptional regulatory sequences.

The present invention also encompasses pharmaceutical compositions of antioxidant salen-manganese complexes, therapeutic uses of such antioxidant salen-manganese complexes, methods and compositions for using antioxidant salen-manganese complexes in diagnostic, therapeutic, and research applications in human and veterinary medicine.

The invention also provides methods for preventing food spoilage and oxidation by applying to foodstuffs an effective amount of at least one antioxidant salen-metal complex species. The invention also provides compositions for preventing food spoilage comprising an effective amount of at least one species of antioxidant salen-metal complex, optionally in combination with at least one additional food preservative agent (e.g., butylated hydroxytoluene, butylated hydroxyanisole, sulfates, sodium nitrite, sodium nitrate). For example, an antioxidant salen-metal complex is incorporated into a foodstuff subject to rancidification (e.g., oxidation) to reduce the rate of oxidative decomposition of the foodstuff when exposed to molecular oxygen.

All publications and patent applications herein are incorporated by reference to the same extent as if each individual publication or patent application was specifically and individually indicated to be incorporated by reference.

DEFINITIONS

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are defined below.

As used herein, an "antioxidant" is a substance that, when present in a mixture or structure containing an oxidizable substrate biological molecule, significantly delays or prevents oxidation of the substrate biological molecule. Antioxidants can act by scavenging biologically important reactive free radicals or other reactive oxygen species ($.O_2^-$, $H_2O_2$, $.OH$, HoCl, ferryl, peroxyl, peroxynitrite, and alkoxyl), or by preventing their formation, or by catalytically converting the free radical or other reactive oxygen species to a less reactive species. An antioxidant salen-transition metal complex of the invention generally has detectable SOD activity. A salen-transition metal complex of the invention has antioxidant activity if the complex, when added to a cell culture or assay reaction, produces a detectable decrease in the amount of a free radical, such as superoxide, or a nonradical reactive oxygen species, such as hydrogen peroxide, as compared to a parallel cell culture or assay reaction that is not treated with the complex. Suitable concentrations (i.e., efficacious dose) can be determined by various methods, including generating an empirical dose-response curve, predicting potency and efficacy of a congener by using QSAR methods or molecular modeling, and other methods used in the pharmaceutical sciences. Since oxidative damage is generally cumulative, there is no minimum threshold level (or dose) with respect to efficacy, although minimum doses for producing a detectable therapeutic or prophylactic effect for particular disease states can be established.

Figure 3:
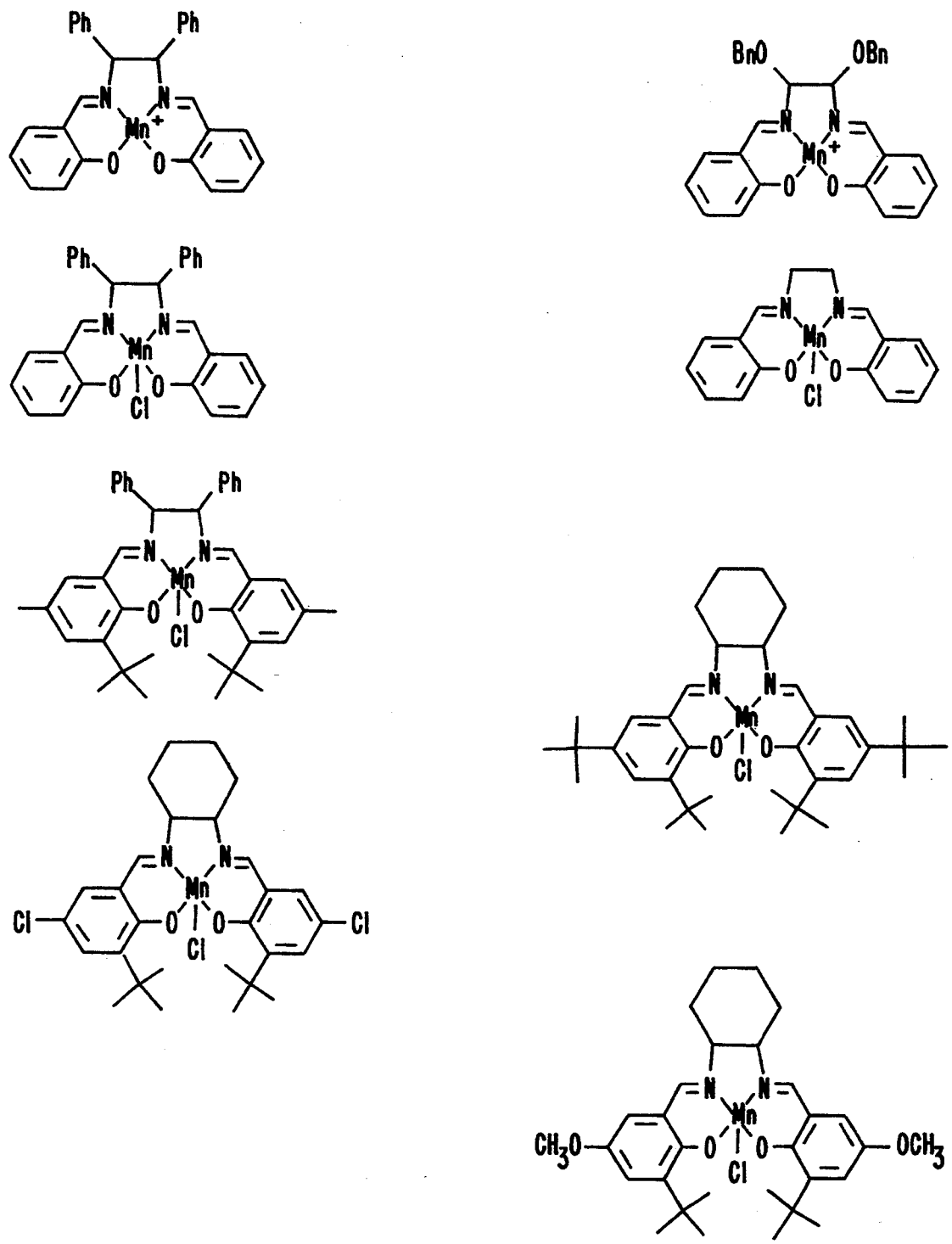
FIG. 3 shows structures of preferred compounds of the invention.

As used herein, a "salen-transition metal complex" refers to a compound having a structure according to Structure I, Structure II, Structure III, or Structure IV, Structure V, Structure VI, Structure VII, Structure VIII, Structure IX (see, infra) or any of the structures C1, C4, C6, C7, C9, C10, C11, C12, C15, C17, C20, C22, C23, C25, C27, C28, C29, and C30 as shown in FIG. 3 and infra, preferably having a structure corresponding to one of the structures shown in FIG. 3 selected from the group consisting of: C6, C7, and C12; more preferably having a structure corresponding to the C7 or C12 structure for catalytic removal of superoxide. The transition metal is typically selected from the group consisting of: Mn, Co, Fe, V, Cr, and Ni; and is most conveniently Mn.

As used herein, "free radical-associated disease" refers to a pathological condition of an individual that results at least in part from the production of or exposure to free radicals, particularly oxyradicals, and other reactive oxygen species in vivo. It is evident to those of skill in the art that most pathological conditions are multifactorial, in that multiple factors contributing to the disease state are present, and that assigning or identifying the predominant causal factor(s) for any individual pathological condition is frequently extremely difficult. For these reasons, the term "free radical associated disease" encompasses pathological states that are recognized in the art as being conditions wherein damage from free radicals or reactive oxygen species is believed to contribute to the pathology of the disease state, or wherein administration of a free radical inhibitor (e.g., desferrioxamine), scavenger (e.g., tocopherol, glutathione), or catalyst (e.g., SOD, catalase) is shown to produce a detectable benefit by decreasing symptoms, increasing survival, or providing other detectable clinical benefits in treating or preventing the pathological state. For example but not limitation, the disease states discussed herein are considered free radical-associated diseases (e.g., ischemic reperfusion injury, inflammatory diseases, systemic lupus erythematosis, myocardial infarction, stroke, traumatic hemorrhage, spinal cord trauma, Crohn's disease, autoimmune diseases (e.g., rheumatoid arthritis, diabetes), cataract formation, uveitis, emphysema, gastric ulcers, oxygen toxicity, neoplasia, radiation sickness, and other pathological states discussed in the Background section and infra).

As used herein the terms "SOD mimetic" "SOD mimic" "superoxide dismutase mimetic", and "superoxide catalyst" refer to compounds which have detectable catalytic activity for the dismutation of superoxide as determined by assay. Generally, an SOD mimetic possesses at least about 0.001 percent of the SOD activity of human Mn-SOD or Zn,Cu-SOD, on a molar basis, as determined by standard assay methods and/or has at least 0.01 unit of SOD activity per mM according to the SOD assay used hereinbelow, preferably at least 1 unit of SOD activity per mM.

The term "alkyl" refers to a cyclic, branched, or straight chain alkyl group containing only carbon and hydrogen, and unless otherwise mentioned, contain one to twelve carbon atoms. This term is further exemplified by groups such as methyl, ethyl, n-propyl, isobutyl, t-butyl, pentyl, pivalyl, heptyl, adamantyl, and cyclopentyl. Alkyl groups can either be unsubstituted or substituted with one or more substituents, e.g., halogen, alkyl, alkoxy, alkylthio, trifluoromethyl, acyloxy, hydroxy, mercapto, carboxy, aryloxy, aryl, arylalkyl, heteroaryl, amino, alkylamino, dialkylamino, morpholino, piperidino, pyrrolidin-1-yl, piperazin-1-yl, or other functionality.

The term "lower alkyl" refers to a cyclic, branched or straight chain monovalent alkyl radical of one to six carbon atoms. This term is further exemplified by such radicals as methyl, ethyl, n-propyl, i-propyl, n-butyl, t-butyl, i-butyl (or 2-methylpropyl), cyclopropylmethyl, i-amyl, n-amyl, and hexyl.

The term "aryl" or "Ar" refers to a monovalent unsaturated aromatic carbocyclic group having a single ring (e.g., phenyl) or multiple condensed rings (e.g., naphthyl or anthryl), which can optionally be unsubstituted or substituted with, e.g., halogen, alkyl, alkoxy, alkylthio, trifluoromethyl, acyloxy, hydroxy, mercapto, carboxy, aryloxy, aryl, arylalkyl, heteroaryl, amino, alkylamino, dialkylamino, morpholino, piperidino, pyrrolidin-1-yl, piperazin-1-yl, or other functionality.

The term "substituted alkoxy" refers to a group having the structure —O—R, where R is alkyl which is substituted with a non-interfering substituent. The term "arylalkoxy" refers to a group having the structure —O—R—Ar, where R is alkyl and Ar is an aromatic substituent. Arylalkoxys are a subset of substituted alkoxys. Examples of preferred substituted alkoxy groups are: benzyloxy, napthyloxy, and chlorobenzyloxy.

The term "aryloxy" refers to a group having the structure —O—Ar, where Ar is an aromatic group. A preferred aryloxy group is phenoxy.

The term "heterocycle" refers to a monovalent saturated, unsaturated, or aromatic carbocyclic group having a single ring (e.g., morpholino, pyridyl or furyl) or multiple condensed rings (e.g., indolizinyl or benzo[b]thienyl) and having at least one heteroatom, defined as N, O, P, or S, within the ring, which can optionally be unsubstituted or substituted with, e.g., halogen, alkyl, alkoxy, alkylthio, trifluoromethyl, acyloxy, hydroxy, mercapto, carboxy, aryloxy, aryl, arylalkyl, heteroaryl, amino, alkylamino, dialkylamino, morpholino, piperidino, pyrrolidin-1-yl, piperazin-1-yl, or other functionality. The term "heteroaryl" or "HetAr" refers to an aromatic heterocycle.

"Arylalkyl" refers to the groups —R—Ar and —R—HetAr, where Ar is an aryl group, HetAr is a heteroaryl group, and R is straight-chain or branched-chain aliphatic group. Examples of arylalkyl groups include benzyl and furfuryl. Arylalkyl groups can optionally be unsubstituted or substituted with, e.g., halogen, alkyl, alkoxy, alkylthio, trifluoromethyl, acyloxy, hydroxy, mercapto, carboxy, aryloxy, aryl, arylalkyl, heteroaryl, amino, alkylamino, dialkylamino, morpholino, piperidino, pyrrolidin-1-yl, piperazin-1-yl, or other functionality.

As used herein, the term "halo" or "halide" refers to fluoro, bromo, chloro and iodo substituents.

As used in the structures that follow, the term "OBn" means benzyloxy.

As used herein, the term "amino" refers to a chemical functionality —NR'R", where R' and R" are independently hydrogen, alkyl, or aryl. The term "quaternary amine" refers to the positively charged group —N$^+$R'R"R'", where R', R", and R'" are independently selected and are alkyl or aryl. A preferred amino group is —NH$_2$.

The term "silyl" as used herein refers to organometallic substituents, wherein at least one silicon atom is linked to at least one carbon atom; an example of a silyl substituent is the trimethylsilyl substituent, (CH$_3$)$_3$Si—.

The term "pharmaceutical agent or drug" as used herein refers to a chemical compound or composition capable of inducing a desired therapeutic effect when properly administered to a patient.

Other chemistry terms herein are used according to conventional usage in the art, as exemplified by *The McGraw-Hill Dictionary of Chemical Terms* (ed. Parker, S., 1985), McGraw-Hill, San Francisco, incorporated herein by reference).

DETAILED DESCRIPTION

Generally, the nomenclature used hereafter and the laboratory procedures in cell culture, analytical chemistry, organic synthetic chemistry, and pharmaceutical formulation described below are those well known and commonly employed in the art. Standard techniques are used for chemical syntheses, chemical analyses, pharmaceutical formulation and delivery, and treatment of patients.

A basis of the present invention is the unexpected finding that members of a class of compounds described originally as epoxidation catalysts, the so-called salen-transition metal complexes, also exhibit potent superoxide dismutase activity and/or catalase activity and function as catalysts for free radical removal both in vitro and in vivo. The salen-transition metal complexes have been described as chiral epoxidation catalysts for various synthetic chemistry applications (Fu et al. (1991) *J. Org. Chem.* 56: 6497; Zhang W. and Jacobsen E. N. (1991) *J. Org. Chem.* 56: 2296; Jacobsen et al. (1991) *J. Am. Chem. Soc.* 113: 6703; Zhang et al. (1990) *J. Am. Chem. Soc.* 112: 2801; Lee N. H. and Jacobsen E. N. (1991) *Tetrahedron Lett.* 32: 6533; Jacobsen et al. (1991) *J. Am. Chem. Soc.* 113: 7063; Lee et al. (1991) *Tetrahedron Lett.* 32: 5055; National Institutes of Health grant GM-43214-01A1; National Science Foundation Grant CHE-9057740; U.S. Ser. Nos. 07/749,460; 07/673,208; each of which is incorporated herein by reference). However, salen-transition metal complexes are also useful as potent antioxidants for various biological applications, including their use as pharmaceuticals for prevention or treatment of free radical-associated diseases. Pharmaceutical formulations, dietary supplements, improved cell and organ culture media, improved cryopreservation media, topical ointments, and chemoprotective and radioprotective compositions can be prepared with an effective amount or concentration of at least one antioxidant salen-transition metal complex species.

The catalytic activity of salen-metal complexes to interconvert epoxides may also be used to advantage to scavenge or prevent formation in vivo of cytotoxic and/or carcinogenic epoxide species, such as may be formed by the cytochrome P-450 monooxygenation system (e.g., benzo-[a]-pyrene diol epoxide). Catalytic salen-metal complexes may be advantageously included into foodstuffs or dietary supplements (or administered in other forms) to individuals who are at risk of exposure to polycyclic hydrocarbon chemical carcinogens, such as workers in the petrochemical industry and dyestuff manufacture. Moreover, catalytically active salen-metal complexes may be formulated for administration to smokers (including passive smokers) to enhance detoxification of reactive epoxides formed from cigarette smoke.

Salen-Transition Metal Complexes

In accordance with a first aspect of the invention, the salen-transition metal complex has the following structure:

Structure I

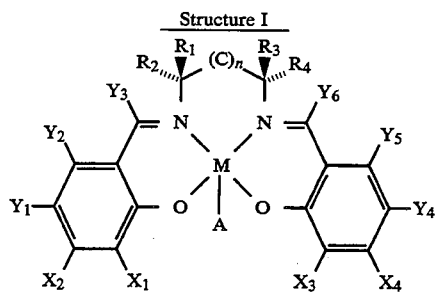

wherein M is a transition metal ion, preferably Mn; A is an anion, typically Cl; and n is either 0, 1, or 2. $X_1$, $X_2$, $X_3$ and $X_4$ are independently selected from the group consisting of hydrogen, silyls, aryls, arylalkyls, primary alkyls, secondary alkyls, tertiary alkyls, alkoxys, aryloxys, aminos, quaternary amines, heteroatoms, and hydrogen; typically $X_1$ and $X_3$ are from the same functional group, usually hydrogen, quaternary amine, or tertiary butyl, and $X_2$ and $X_4$ are typically hydrogen. $Y_1$, $Y_2$, $Y_3$, $Y_4$, $Y_5$, and $Y_6$ are independently selected from the group consisting of hydrogen, halides, alkyls, aryls, arylalkyls, silyl groups, aminos, alkyls or aryls bearing heteroatoms; aryloxys, alkoxys, and halide; preferably, $Y_1$ and $Y_4$ are alkoxy, halide, or amino groups. Typically, $Y_1$ and $Y_4$ are the same. $R_1$, $R_2$, $R_3$ and $R_4$ are independently selected from the group consisting of H, $CH_3$, $C_2H_5$, $C_6H_5$, O-benzyl, primary alkyls, fatty acid esters, substituted alkoxyaryls, heteroatom-bearing aromatic groups, arylalkyls, secondary alkyls, and tertiary alkyls.

According to one class of embodiments of the first aspect of the invention, at least one of the $X_1$ and $X_3$ sites, and preferably both $X_1$ and $X_3$ include a substituent selected from the group of blocking substituents consisting of secondary or tertiary alkyl groups, aryl groups, silyl groups, heterocycles, and alkyl groups bearing heteroatom substituents such as alkoxy or halide. Preferably, the $X_1$ and $X_3$ sites bear the same substituent, which substituent is most preferably a tertiary alkyl group, such as tertiary butyl. Preferably, when $X_1$ and $X_3$ bear a blocking substituent, then $X_2$ and $X_4$ are selected from a group of non-blocking substituents such as H, $CH_3$, $C_2H_5$, and primary alkyls, most preferably, H. Alternatively, either three or four of $X_1$, $X_2$, $X_3$, and $X_4$ can be selected from the group of blocking substituents.

According to this first aspect of the invention, typically at least one and generally no more than two of $R_1$, $R_2$, $R_3$ and $R_4$ are selected from a group consisting of H, $CH_3$, $C_2H_5$, and primary alkyls. For convenience, this group will be referred to as the non-blocking group. If $R_1$ is selected from the non-blocking group, then $R_2$ and $R_3$ are preferably selected from the blocking group, and typically $R_2$ and $R_3$ are identical and are phenyl or benzyloxy. If $R_2$ is selected from the non-blocking group, then $R_1$ and $R_4$ are preferably selected from the blocking group. Likewise, if $R_3$ is selected from the non-blocking group, then $R_1$ and $R_4$ are preferably selected from the blocking group. Finally, if $R_4$ is selected from the non-blocking group, then $R_2$ and $R_3$ are preferably selected from the blocking group. Phenyl and benzyloxy are particularly preferred blocking groups for substitution at any of $R_1$, $R_2$, $R_3$ and $R_4$. Typically, the blocking groups selected are identical. A preferred class of embodiments have $R_1$ and $R_4$ as benzyloxy or phenyl and $R_2$ and $R_3$ as hydrogen.

Stated in other terms, one class of embodiments of the first aspect of the invention requires that, of the four sites available for substitution on the two carbon atoms adjacent to nitrogen, at least one or two of these preferably will include a substituent from the non-blocking group.

Preferably, the non-blocking substituent is either hydrogen or methyl, but most preferably, hydrogen.

Preferably, the blocking substituent is either a phenyl group, a benzyloxy, or a tertiary butyl group, more preferably a phenyl group or a benzyloxy group, most usually a phenyl group.

Preferably, $Y_3$ and $Y_6$ are hydrogen, methyl, alkyl, or aryl. More preferably, they are hydrogen or methyl. Most preferably, they are hydrogen.

The $Y_1$, $Y_2$, $Y_4$, and $Y_5$ sites are selected independently and are preferably occupied by hydrogen, although these sites may also be occupied by substituents independently selected from the group consisting of hydrogen, halides, alkyls, aryls, alkoxy groups, substituted alkoxy groups, nitro groups, and amino groups. $Y_1$ and $Y_4$ are preferably occupied by methoxy, ethoxy, chloro, bromo, iodo, primary alkyl, tertiary butyl, primary amine, secondary amine, or tertiary amine substituents, most preferably methoxy, chloro, tertiary butyl, or methyl.

In accordance with a second aspect of the invention, the salen-transition metal complex has the structure:

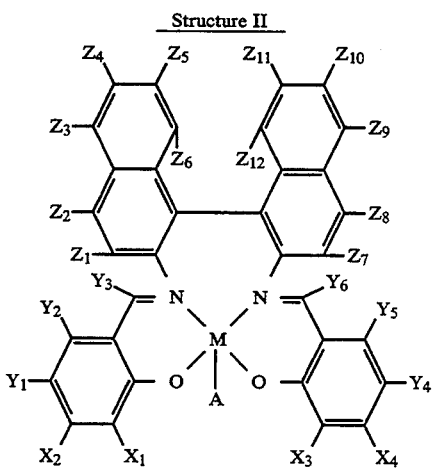

Structure II wherein M is a transition metal ion, preferably Mn, and A is an anion, typically Cl; where at least one of $X_1$ or $X_2$ is selected from the group consisting of aryls, primary alkyls, secondary alkyls, tertiary alkyls, and heteroatoms; where at least one of $X_1$ or $X_3$ is selected from the group consisting of aryls, primary alkyls, secondary alkyls, tertiary alkyls, arylalkyls, heteroatoms, and hydrogen, preferably tertiary butyl or hydrogen; and where $Y_1$, $Y_2$, $Y_3$, $Y_4$, $Y_5$, $Y_6$, $Z_1$, $Z_2$, $Z_3$, $Z_4$, $Z_5$, $Z_6$, $Z_7$, $Z_8$, $Z_9$, $Z_{10}$, $Z_{11}$, and $Z_{12}$ are independently selected from the group consisting of hydrogen, halides, alkyls, aryls, amines, alkoxy, substituted alkoxy, arylalkyls, aryloxys, and alkyl groups bearing heteroatoms. Preferably $Y_1$ and $Y_4$ are selected from the group consisting of lower alkyls, alkoxy, halide, and amino groups, more preferably from the group consisting of methoxy, chloro, and primary amine. One preferred embodiment according to this second aspect is the species where: $Y_1$ and $Y_4$ are methoxy: $X_1$ and $X_3$ are independently selected and are hydrogen or tertiary butyl, and the remaining substituents are hydrogen.

In accordance with a third aspect of the invention, the salen-transition metal has the following structure:

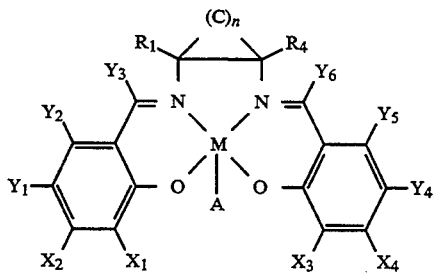

Structure III where M is a transition metal ion, typically Mn, and A is an anion, typically Cl; where n is either 4, 5, or 6; where $X_1$, $X_2$, $X_3$, and $X_4$ are independently selected from the group consisting of aryls, arylalkyls, aryloxys, primary alkyls, secondary alkyls, tertiary alkyls, alkoxy, substituted alkoxy, heteroatoms, aminos, quaternary amines, and hydrogen; preferably, at least one of $X_1$ or $X_3$ are selected from the group consisting of aryls, primary alkyls, secondary alkyls, tertiary alkyls, quaternary amines, arylalkyls, heteroatoms, and hydrogen; preferably $X_1$ and $X_3$ are identical and are hydrogen or tertiary butyl; where $Y_1$, $Y_2$, $Y_3$, $Y_4$, $Y_5$, and $Y_6$ are selected from the group consisting of aryls, arylalkyls, primary alkyls, secondary alkyls, tertiary alkyls, alkoxys, substituted alkoxys, aryloxys, halides, heteroatoms, aminos, quaternary amines, and hydrogen; preferably at least one of $Y_1$ or $Y_4$ are selected from the group consisting of aryls, primary alkyls, secondary alkyls, tertiary alkyls, substituted alkoxy, heteroatoms, amines, and halides; more preferably $Y_1$ and $Y_4$ are identical and are either methoxy, chloro, bromo, iodo, tertiary butyl, or amine. $R_1$ and $R_4$ are independently selected from the group consisting of hydrogen, halides, primary alkyls, secondary alkyls, tertiary alkyls, fatty acid esters, alkoxys, or aryls. Preferably $R_1$ and $R_4$ are identical; more preferably $R_1$ and $R_4$ are hydrogen.

Preferred Antioxidant Salen-Metal Species

The following genera of antioxidant salen-metal complexes are preferred for use in the compositions and methods of the present invention, where substituents are not shown they are hydrogen:

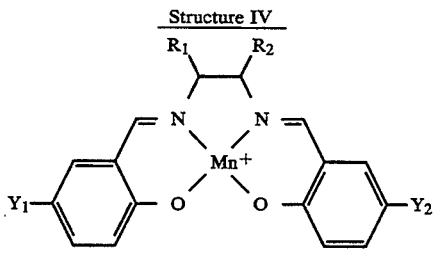

Structure IV where $Y_1$ and $Y_2$ are independently selected from the group consisting of methoxy, ethoxy, methyl, ethyl, t-butyl, chloro, bromo, iodo, amino, quaternary amine, alkylamino, dialkylamino, and hydrogen $R_1$ and $R_2$ are selected independently from the group consisting of: phenyl benzyloxy, chlorobenzyloxy, hydrogen, amino, quaternary amine, or fatty acid ester. Preferably, $Y_1$ and $Y_2$ are identical.

Structure V

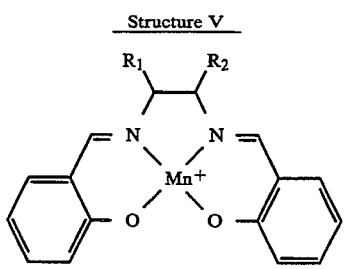

where $R_1$ and $R_2$ are selected independently from the group consisting of: phenyl, benzyloxy, chlorobenzyloxy, hydrogen, amino, quaternary amine, or fatty acid ester. Preferably, $R_1$ and $R_2$ are identical.

Structure VI

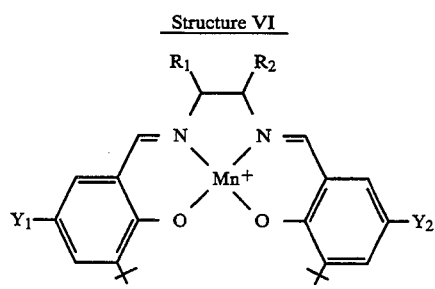

where $Y_1$ and $Y_2$ are independently selected from the group consisting of methoxy, ethoxy, methyl, ethyl, t-butyl, chloro, bromo, iodo, amino, quaternary amine, alkylamino, dialkylamino, and hydrogen; $R_1$ and $R_2$ are selected independently from the group consisting of: phenyl, benzyloxy, chlorobenzyloxy, hydrogen, amino, quaternary amine, or fatty acid ester. Preferably, $Y_1$ and $Y_2$ are identical, and $R_1$ and $R_2$ are identical.

Structure VII

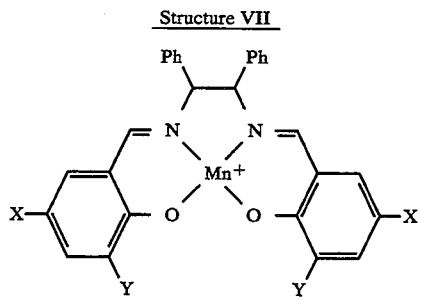

where X is selected from the group consisting of methoxy, ethoxy, methyl, ethyl, t-butyl, chloro, bromo, iodo, amino, quaternary amine, alkylamino, dialkylamino, and hydrogen; Y is selected from the group consisting of t-butyl, quaternary amine, amino, and hydrogen.

Structure VIII

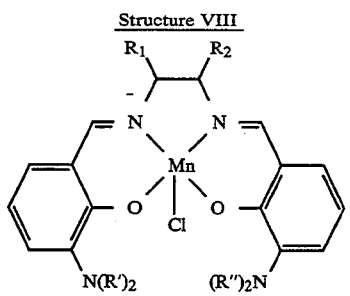

where $R_1$ and $R_2$ are independently selected from the group consisting of aryloxys, alkoxys, aryls, and hydrogen; R' and R" are independently selected from the group consisting of alkyls, aryls, and hydrogen. Preferably, at least one of the amino groups is protonated at physiological pH (i.e., pH 7.3–7.8).

A preferred subgenus of Structure VIII includes, but is not limited to:

Structure IX

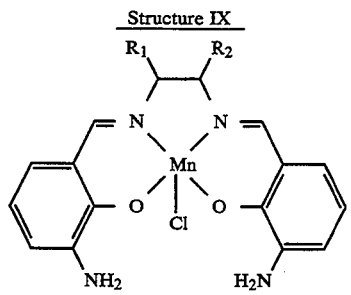

where R, and $R_2$ are independently selected from the group consisting of alkyls and hydrogen. Preferably, at least one of the amino groups are protonated at physiological pH (i.e., pH 7.3–7.8).

The following species are preferred antioxidant salen-transition metal complexes for formulation in pharmaceutical compositions, dietary supplements, foodstuff preservatives, cosmetics, sunburn preventatives, and other compositions of the invention, and are referenced by structure number (e.g., C1 through C30) for clarity throughout.

C1:

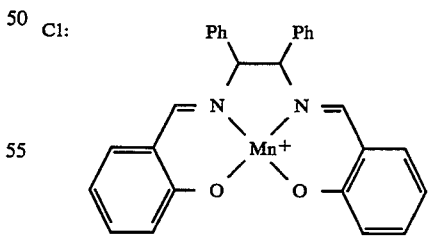

C4:

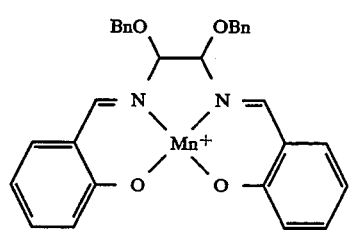

-continued
C6: 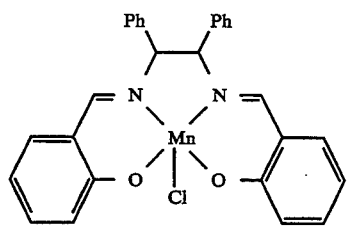
C7: 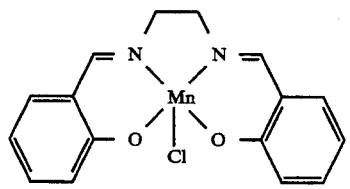
C9: 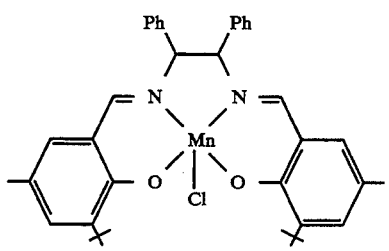
C10: 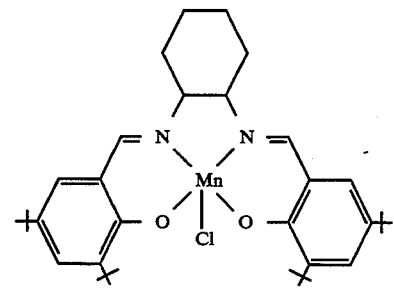
C11: 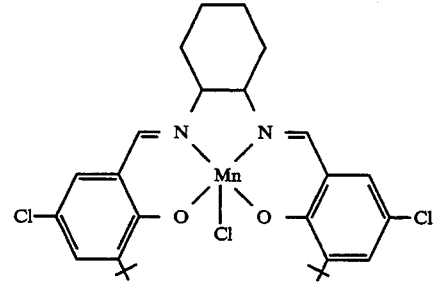
C12: 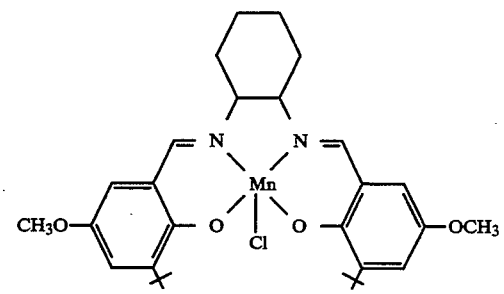
-continued
C15: 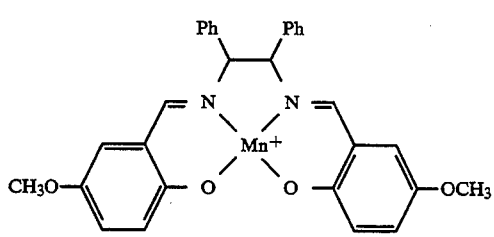
C17: 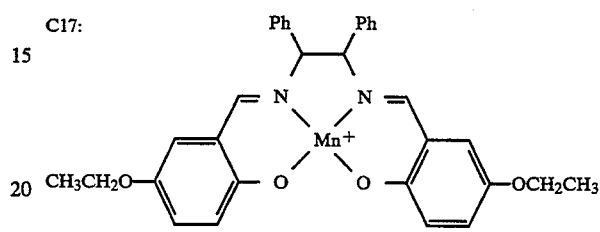
C20: 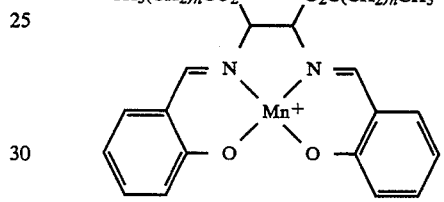
C22: 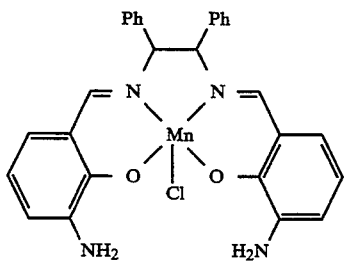
C23: 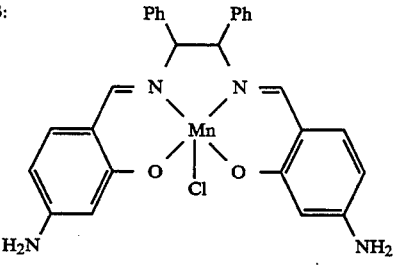
C25: 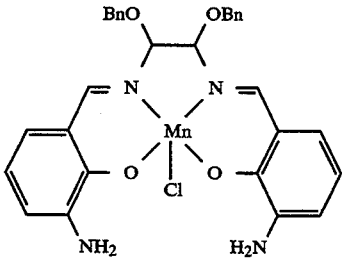

C27:

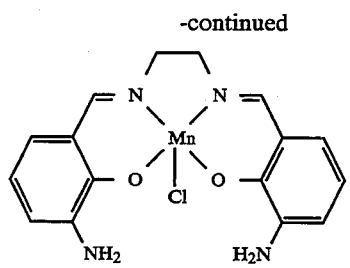

C28:

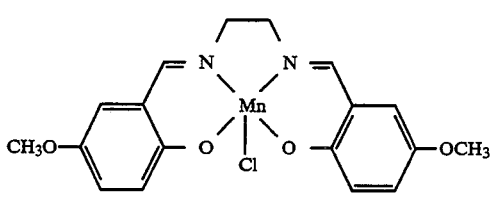

Pharmaceutical Compositions

Figure 1:
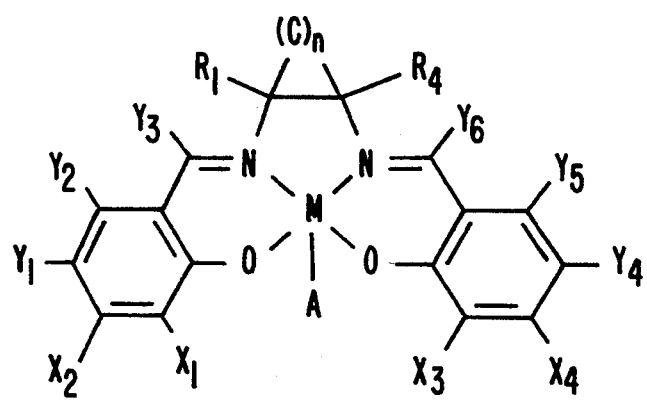
FIG. 1 shows the general structure of salen derivatives of the invention.
Figure 2:
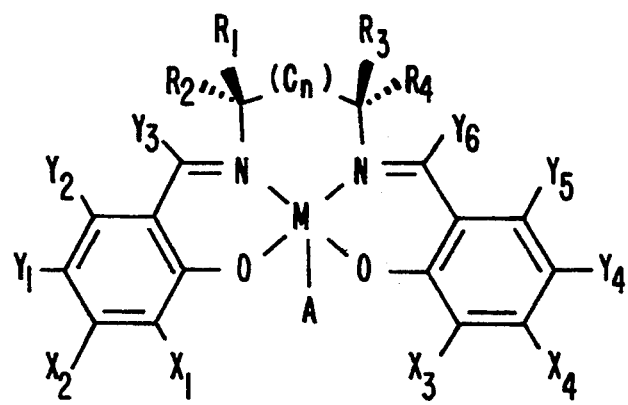
FIG. 2 shows a salen derivative according to the structure shown in FIG. 1, wherein n is 0.

The preferred pharmaceutical compositions of the present invention comprise a therapeutically or prophylactically effective dose of at least one salen derivative-based complex of a transition metal ion. The term "salen" is used herein to refer to those ligands typically formed through a condensation reaction of two molecules of a salicylaldehyde derivative with one molecule of a diamine derivative. While salen ligands are formed from ethylenediamine derivatives, propyl and butyl diamines may also be used to give analogous salen and salen derivatives. Salen derivatives are preferred and their general structure is shown in FIG. 1. A salen derivative where n is 0 is shown in FIG. 2.

As seen in FIG. 1, the two nitrogens and the two oxygens are oriented toward the center of the salen ligand and thus provide a complexing site for the transition metal ion M. Preferably, this metal ion is selected from the group consisting of Mn, Cr, Fe, Ni, Co, Ti, V, Ru, and Os. More preferably, the transition metal ion is selected from the group consisting of Mn, Cr, Fe, Ni, and Co. Most preferably, the metal ion is Mn.

Preferably, the anion is selected from the group consisting of Mn, Cr, Fe, Ni, Co, Ti, V, Ru, and Os. More the metal ion is Mn.

Preferably, the anion is selected from the group consisting of $PF_6$, (aryl)$_4$, $BF_4$, B(aryl)$_4$, halide, acetate, triflate, tosylate, with halide or $PF_6$ being more preferred, and chloride being most preferred.

FIG. 1 also shows the many sites available for substitution on the salen ligand. Of these sites, it is believed that $R_1$, $R_2$, $R_3$, $R_4$, and $X_1$, $X_2$, $X_3$, $X_4$, $Y_3$ and $Y_6$ are the most important in this first salen-transition metal complex.

TABLE I

| $CH_3-(CH_2)_f-(CH=CH)_g-(CH_2)_h-CO_2H$ | | | | |
|---|---|---|---|---|
| Carbons | f | g | h | Acid Name |
| 16 | 5 | 1 | 7 | Palmitoleic |
| 18 | 7 | 1 | 7 | Oleic |
| 18 | 10 | 1 | 4 | Petroselenic |
| 18 | 5 | 1 | 9 | Vaccenic |
| 18 | 3 | 3 | 7 | Punicic |
| 18 | 1 | 4 | 7 | Parinaric |
| 20 | 9 | 1 | 7 | Gadoleic |
| 22 | 9 | 1 | 9 | Cetoleic |

TABLE II

| $CH_3-(CH_2)_f-(CH=CH-CH_2)_m-(CH_2)_p-CO_2H$ | | | | |
|---|---|---|---|---|
| Carbons | f | g | h | Acid Name |
| 18 | 4 | 2 | 6 | Linoleic |
| 18 | 1 | 3 | 6 | Linolenic |
| 20 | 4 | 4 | 2 | Arachidonic |

TABLE III

| $CH_3-(CH_2)_w-CO_2H$ | | |
|---|---|---|
| Carbons | w | Acid Name |
| 12 | 10 | Lauric |
| 14 | 12 | Myristic |
| 16 | 14 | Palmitic |
| 18 | 16 | Stearic |
| 20 | 18 | Eicosanoic |
| 22 | 20 | Docosanoic |

It will be appreciated that the unsaturated acids occur in isomeric forms due to the presence of the one or more unsaturated positions. The compounds of the present invention are intended to include the individual double bond isomers, as well as mixtures thereof. The fatty acid esters of the present invention can be obtained by known acylation techniques. See, e.g., March, *Advanced Organic Chemistry*, 3rd Ed., John Wiley & Sons, New York (1985), pp. 299, 348–351, and 353–354, incorporated herein by reference.

Preferred Antioxidant Salen-Transition Metal Complexes

FIG. 3 shows structures of preferred antioxidant salen-transition metal complexes of the invention. Example antioxidant salen-transition metal complexes are shown in FIG. 3. Compounds C1, C4, C6, C7, C9, C10, C11, and C12 are particularly preferred for formulation in pharmaceuticals and other antioxidant compositions of the invention. It is believed that C7 is particularly preferred because of its facile preparation and relatively hydrophilic nature which is well-suited to pharmaceutical usage.

A preferred salen-transition metal complex having high superoxide dismutase activity is the C12 compound having the structure:

C12:

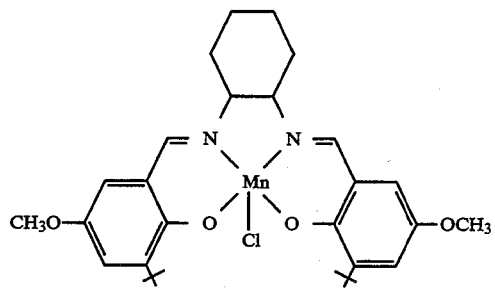

additional preferred congeners of C12 are:

C29:

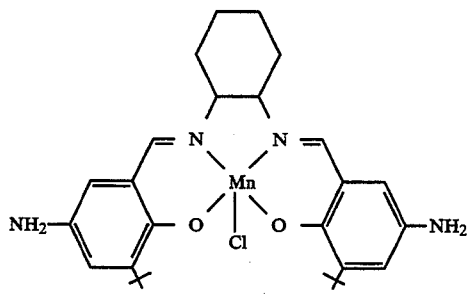

and

C30:

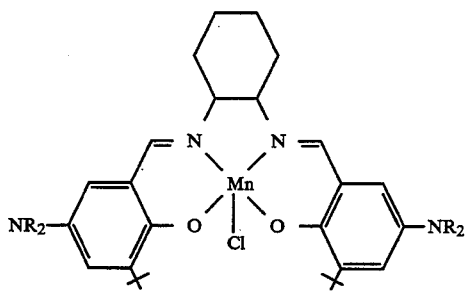

A particularly preferred antioxidant salen-metal complex of the invention is C7:

C7:

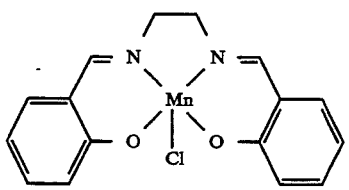

Antioxidant salen-transition metal complexes generally have detectable superoxide dismutase activity and preferably also have catalase activity. Advantageously, C7 is both simple to prepare and relatively hydrophilic, properties which make it particularly well-suited for pharmaceutical use and formulation in aqueous solution. The relatively hydrophilic nature of C7 can be used to advantage in providing antioxidant salen-metal complexes that are readily absorbed and transported in the human body. One advantageous pharmacokinetic property of C7 is believed to be the capacity to cross the blood-brain barrier efficiently.

Preparation of Antioxidant Salen-Transition Metal Complexes

Preparation of salen-transition metal complexes are performed essentially as described in National Institutes of Health grant GM-43214-01A1; National Science Foundation Grant CHE-9057740; U.S. Ser. No. 07/809,446 filed Dec. 16, 1991, U.S. Ser. No. 07/749,460 filed Aug. 26, 1991; U.S. Ser. No. 07/673,208 filed Mar. 21, 1991; US91/01915 filed Mar. 21, 1991, Fu et al. (1991) *J. Org. Chem.* 56: 6497; Zhang W. and Jacobsen E. N. (1991) *J. Org. Chem.* 56: 2296; Jacobsen et al. (1991) *J. Am. Chem. Soc.* 113: 6703; Zhang et al. (1990) *J. Am. Chem. Soc.* 112: 2801; Lee N. H. and Jacobsen E. N. (1991) *Tetrahedron Lett.* 32: 6533; Jacobsen et al. (1991) *J. Am. Chem. Soc.* 113: 7063; Lee et al. (1991) *Tetrahedron Lett.* 32: 5055, each of which is incorporated herein by reference.

Generally, the preferred route to prepare the antioxidant salen-transition metal complexes of the present invention is a condensation reaction with the substituted salicylaldehyde and the substituted diamine. In general, quantities of these compounds are reacted in a 2 to 1 molar ration in absolute ethanol. The solutions are refluxed typically for 1 hour, and the salen ligand is either precipitated in analytically pure form by addition of water, or the metal complex is generated directly by addition of the metal as its acetate, halide, or triflate salt.

The following procedure is general for the preparation of antioxidant salen-Mn complexes of the formula:

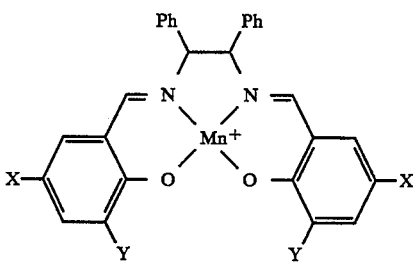

The salen ligand is redissolved in hot absolute ethanol to give a 0.1M solution. Solid $Mn(OAC)_2 \cdot 4H_2O$ (2.0 equivalents) is added in one portion and the solution is refluxed for 1 h. Approximately 3 equivalents of solid LiCl are then added and the mixture is heated to reflux for an additional 0.5 h. Cooling the mixture to 0° C. affords the Mn(III) complex as dark brown crystals which are washed thoroughly with $H_2O$ and isolated by filtration in approximately 75% yield. An additional crop of material can be obtained by dropwise addition of $H_2O$ to the mother liquor. Combined yields of catalyst are typically about 80–95% for this step, and about at least 80–90% overall from the optically pure 1,2-diphenylethylene diamine.

Another example of the method of preparing the antioxidant salen-Mn complexes are described as follows: Most preferably, the starting diamine is R,R- or S,S-1,2-diamino-1,2-diphenylethane and the starting salicylaldehyde is 3-tertbutylsalicylaldehyde. A solution of 2.0 mmol of 3-tertbutylsalicylaldehyde in 3 ml of absolute ethanol is added dropwise to a solution of 1.0 mmol of (R,R)-1,2-diamino-1,2-diphenylethane in 5 ml of ethanol. The reaction mixture is heated to reflux for 1h and then 1.0 mmol of $Mn(Oac)_2 \cdot 4H_2O$ is added in one portion to the hot (60° C.) solution. The color of the solution immediately turns from yellow to brown upon addition. It is refluxed for an additional 30 min and then cooled to room temperature. A solution of 10% NaCl (5ml) is then added dropwise and the mixture stirred for 0.5 h. The solvents are then removed in vacuo and the residue is triturated with 50 ml of $CH_2$—$Cl_2$ and 50 ml of $H_2O$. The organic layer is separated and the brown solution is washed with saturated NaCl. Separation of the organic phase and removal of solvent resulted in a crude material which can be recrystallized from $C_6H_6/C_6H_{14}$ to give a (R,R)-salen-Mn complex.

The synthesis of the antioxidant salen-transition metal complexes of the invention may be routinely accomplished by those of ordinary skill in the art according to the cited publications.

The SOD activity of the prepared salen-Mn complexes is determined according to standard assay methods for SOD activity known in the art and exemplified infra. Salen-metal complexes having at least 0.01 unit of SOD activity per millimole/liter in aqueous solution are antioxidant salen-metal complexes; preferably antioxidant salen-metal complexes have at least about 1 unit of SOD activity per millimole/liter; and more preferably have at least about 100 units of SOD activity per millimole/liter; frequently having more that 500 to 1000 units of SOD activity per mM or more. For some medical uses where catalase activity is preferably supplemented, it is advantageous that the SOD mimetic salen-metal complex also possesses detectable catalase activity (e.g., C4, C7, C9, C10, C11, C12); typically at least 10 units of catalase activity per mM, and frequently at least 100 units of catalase activity per mM.

Pharmaceutical Formulations

Pharmaceutical compositions comprising an antioxidant salen-transition metal complex of the present invention are useful for topical and parenteral administration, i.e., subcutaneously, intramuscularly or intravenously. The finding that salen-metal complexes possess SOD activity in vitro as well as functioning in vivo indicates that antioxidant salen-metal complexes are suitable SOD mimetics for pharmaceutical use. The antioxidant salen-metal complexes are suitable for administration to mammals, including human patients and veterinary patients.

The compositions for parenteral administration will commonly comprise a solution of an antioxidant salen-transition metal complex or a cocktail thereof dissolved in an acceptable carrier, preferably an aqueous carrier. Since many of the salen-Mn complexes of the invention are lipophilic, it is preferable to include in the carrier a hydrophobic base (e.g., polyethylene glycol, Tween 20). A variety of aqueous carriers can be used, e.g., water, buffered water, 0.4% saline, 0.3% glycine and the like. These solutions are sterile and generally free of particulate matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example sodium acetate, sodium chloride, potassium chloride, calcium chloride, sodium lactate, etc. The concentration of the antioxidant salen-transition metal complex(es) in these formulations can vary widely, i.e., from less than about 1 nM, usually at least about 0.1 mM to as much as 100 mM and will be selected primarily based on fluid volumes, viscosities, etc., in accordance with the particular mode of administration selected. Most usually, the antioxidant salen-metal complex is present at a concentration of 0.1 mM to 10 mM. For example, a typical formulation for intravenous injection comprises a sterile solution of an antioxidant salen-metal complex (e.g., C7) at a concentration of 5 mM in Ringer's solution. The generally hydrophobic nature of some of the preferred antioxidant salen-metal complexes indicates that a hydrophobic vehicle may be used, or that an aqueous vehicle comprising a detergent or other lipophilic agent (e.g., Tween, NP-40, PEG); alternatively, the antioxidant salen complexes may be administered as a suspension in an aqueous carrier, or as an emulsion.

Thus, a typical pharmaceutical composition for intramuscular injection could be made up to contain 1 ml sterile buffered water, and about 1–100 mg of antioxidant salen-transition metal complex(es). A typical composition for intravenous infusion can be made up to contain 250 ml of sterile Ringer's solution, and about 100–1000 mg of antioxidant salen-transition metal complex(es). Lipophilic agents may be included in formulations of lipophilic salen-metal complexes. Actual methods for preparing parenterally administrable compositions will be known or apparent to those skilled in the art and are described in more detail in, for example, *Remington's Pharmaceutical Science*, 15th Ed., Mack Publishing Company, Easton, Pa. (1980), which is incorporated herein by reference. A typical pharmaceutical composition for topical application can be made with suitable dermal ointments, creams, lotions, ophthalmic ointments and solutions, respiratory aerosols, and other excipients. Excipients should be chemically compatible with the antioxidant salen-transition metal complex(es) that are the active ingredient(s) of the preparation, and generally should not increase decomposition, denaturation, or aggregation of active ingredient(s). Frequently, excipients will have lipophilic components such as oils and lipid emulsions.

The antioxidant salen-transition metal complex(es) of this invention can be lyophilized for storage and reconstituted in a suitable carrier prior to use. It will be appreciated by those skilled in the art that lyophilization and reconstitution can lead to varying degrees of antioxidant activity loss, and that use levels may have to be adjusted to compensate.

The compositions containing the present antioxidant salen-transition metal complex(es) or cocktails thereof can be administered for prophylactic and/or therapeutic treatments. In therapeutic application, compositions are administered to a patient already affected by the particular free radical-associated disease, in an amount sufficient to cure or at least partially arrest the condition and its complications. An amount adequate to accomplish this is defined as a "therapeutically effective dose" or "efficacious dose." Amounts effective for this use will depend upon the severity of the condition, the general state of the patient, and the route of administration, but generally range from about 1 mg to about 10 g of antioxidant salen-transition metal complex(es) per dose, with dosages of from 10 mg to 2000 mg per patient being more commonly used. For example, for treating acute myocardial ischemia/reoxygenation episodes, about 100 to 1000 mg of a antioxidant salen metal complex (e.g., C7) may be administered systemically by intravenous infusion; at least about 10 mg to 500 mg of antioxidant salen-metal complex(es) may be administered by intrapericardial injection to provide elevated local concentrations of SOD activity in the myocardium.

In prophylactic applications, compositions containing the antioxidant salen-transition metal complex(es) or cocktails thereof are administered to a patient not already in a disease state to enhance the patient's resistance or to retard the progression of disease. Such an amount is defined to be a "prophylactically effective dose." In this use, the precise amounts again depend upon the patient's state of health and general level of immunity, but generally range from 1 mg to 10 g per dose, especially 10 to 1000 mg per patient. A typical formulation of an antioxidant salen-metal complex such as C7 will contain between about 25 and 250 mg of the salen-metal complex in a unit dosage form.

Single or multiple administrations of the compositions can be carried out with dose levels and dosing pattern being selected by the treating physician. In any event, the pharmaceutical formulations should provide a quantity of the antioxidant salen-transition metal complex(es) of this invention sufficient to effectively treat the patient.

Kits can also be supplied for use with the subject antioxidant salen-transition metal complex(es) for use in the protection against or therapy for a free radical-associated disease. Thus, the subject composition of the present invention may be provided, usually in a lyophilized form or aqueous solution in a container, either alone or in conjunction with additional antioxidant salen-transition metal complex(es) of the desired type. The antioxidant salen-transition metal complex(es) are included in the kits with buffers, such as Tris, phosphate, carbonate, etc., stabilizers, biocides, inert proteins, e.g., serum albumin, or the like, and a set of instructions for use. Generally, these materials will be present in less than about 5% wt. based on the amount of antioxidant salen-transition metal complex(es), and usually present in total amount of at least about 0.001% based again on the concentration. Frequently, it will be desirable to include an inert extender or excipient to dilute the active ingredients, where the excipient may be present in from about 1 to 99.999% wt. of the total composition.

Salen-Mn complexes, preferably compound C12 or C7, can be incorporated into a hypothermic cardioplegia solution at a concentration of at least about 1 mM into a solution formulation according to Amano et al. (1982) *Jpn. J. Surg.* 12: 87, incorporated herein by reference. Most preferably, C7 is included in the cardioplegia solution.

The dosage of SOD-mimetic salen-metal complex(es) will vary with each particular application. Typically, the composition is administered either systemically or topically. Systemic administration includes per os and parenteral routes; topical administration includes in situ applications. The in situ means includes, for example, administering an SOD-mimetic salen-metal complex by endoscopic bolus wash and/or paravenous injection, or in the case of lower GI treatments, by enema. Parenteral routes may include, for example, subcutaneous, intradermal, intramuscular, and intravenous routes. The amount of SOD-mimetic salen-metal complex(es) will range from about 2 to 5,000 mg or more, typically 10 to 1000 mg, depending on the administration interval and route, which can range from a single oral dose, parenteral dose and/or topical dose to multiple oral doses, parenteral doses, and/or topical doses over a few days or greater than 5 weeks. The dosage may also vary with the severity of the disease.

In Vitro and Research Administration

In another aspect of the invention, antioxidant salen-transition metal complexes of the invention are employed to modulate the expression of naturally-occurring genes or other polynucleotide sequences under the transcriptional control of an oxidative stress response element (e.g., an antioxidant responsive element, ARE), such as an antioxidant response element of a glutathione S-transferase gene or a NAD(P)H:quinone reductase gene (Rozen et al. (1992) *Arch. Biochem. Biophys.* 292: 589; Favreau and Pickett (1991) *J. Biol. Chem.* 266: 4556; Rushmore and Pickett (1991) *Methods Enzymol.* 206: 409; Rushmore and Pickett (1990) *J. Biol. Chem.* 265: 14648; Keyse et al. (1992) *Nature* 359: 644, incorporated herein by reference). Transgenes, homologous recombination constructs, and episomal expression systems (e.g., viral-based expression vectors) comprising a polynucleotide sequence under the transcriptional control of one or more ARE linked to a promoter will be made by those of skill in the art according to methods and guidance available in the art, as will transformed cells and transgenic nonhuman animals harboring such polynucleotide constructs. The antioxidant salen-metal complexes may be used to modulate the transcription of ARE-regulated polynucleotide sequences in cell cultures (e.g., ES cells) and in intact animals, particularly in transgenic animals wherein a transgene comprises one or more AREs as transcriptional regulatory sequences. For transformed or transgenic cell cultures, a dose-response curve is generated by titrating transcription rate of the ARE-controlled polynucleotide sequence against increasing concentrations of antioxidant salen-metal complex(es), which will reduce the transcription rate induced by oxidant agents (e.g., benzoyl peroxide, glutathione-depleting agent) or oxidative stress. Conversely, high levels of SOD-mimetic salen-metal complexes may produce oxidative stress and free radical generation. Similar dose-response titration can be performed in transgenic animals, such as transgenic mice, harboring an ARE-controlled transgene sequence.

In Vivo Administration

According to this invention, a therapeutically or pharmaceutically effective amount of an antioxidant salen-transition metal complex is administered to a patient to treat or prevent a free radical-associated disease. The required dosage will depend upon the nature of the free radical-associated disease, the severity and course of the disease, previous therapy, the patient's health status and response to the antioxidant salen-transition metal complex, and the judgment of the treating physician. Typically, at least one species of antioxidant salen-Mn complex is administered as the sole active ingredient, or in combination with one or more other active ingredients, typically selected from the group consisting of: N-2-mercaptopropionylglycine, N-acetylcysteine, glutathione, dimethyl thiourea, desferrioxamine, mannitol, α-tocopherol, ascorbate, allopurinol, 21-aminosteroids, calpain inhibitors, glutamate receptor antagonists, tissue plasminogen activator, streptokinase, urokinase, nonsteroidal anti-inflammatory agent, cortisone, and carotenoids. Antioxidant salen-Mn complexes may also be administered in conjunction with polypeptides having SOD and/or catalase activity, particularly in view of the capacity of the salen-Mn complexes, unlike SOD polypeptides, to cross the blood-brain barrier and thereby complement systemic SOD administration.

The present invention includes a method of treating patients, such as humans, who have a free radical-associated disease with a prophylactically effective or therapeutically effective amount of a antioxidant salen-transition metal complex, typically a salen-Mn complex, preferably C7. This method can be used to treat patients at various stages of their diseases or to prevent development of free radical-associated diseases in patients. In addition, the treatment can be administered to prevent or reduce, as a prophylactic, the age-adjusted probability of developing a neoplasm and/or the age-adjusted mortality rate and/or the rate of senescence.

The antioxidant salen-metal complexes of the invention can also be administered to patients who are infected with a human immunodeficiency virus (e.g., HIV-1) or who are at risk of becoming infected with a human immunodeficiency virus. The antioxidant salen-metal complexes, typified by C7, can prevent or inhibit the induction of HIV-1 replication in CD4+ lymphocytes by tumor necrosis factor (TNF) and/or prevent damage to or death of CD4+ cells as a consequence of HIV-1 infection. Without wishing to be bound by any particular theory of HIV-1 replication or HIV-1 pathogenesis, it is believed that administration of an antioxidant salen-metal complex, such as C7, can inhibit and/or slow the development of HIV-1 related pathology and/or can reduce the rate of decline of the CD4+ lymphocyte population in HIV-infected individuals. The antioxidant salen-metal complexes, such as C7, can also inhibit pathology resulting from excessive or inappropriate levels of TNF, both in AIDS and in other conditions (e.g., septic shock). Frequently, a dosage of about 50 to 5000 mg will be administered to a patient with HIV and/or with excessive or inappropriate levels of TNF, either in single or multiple doses, to reduce or retard the development of pathology and clinical symptoms. Antioxidant salen-metal complexes may be administered therapeutically to treat viral diseases other than HIV.

Since oxidative damage occurs proportionately to the abundance of free radicals and reactive oxygen species, it is expected that administration of antioxidant salen-transition metal complexes at even low levels will confer a protective effect against oxidative damage; thus it is expected that there is no threshold level below which antioxidant salen-Mn complexes are ineffective.

In general for treatment of free radical-associated diseases, a suitable effective dose of the antioxidant salen-Mn complex will be in the range of 0.01 to 1000 milligram (mg) per kilogram (kg) of body weight of recipient per day, preferably in the range of 1 to 100 mg per kg of body weight per day. The desired dosage is preferably presented in one, two, three, four or more subdoses administered at appropriate intervals throughout the day. These subdoses can be administered as unit dosage forms, for example, containing 5 to 10,000 mg, preferably 10 to 1000 mg of active ingredient per unit dosage form.

The composition used in these therapies can be in a variety of forms. These include, for example, solid, semi-solid and liquid dosage forms, such as tablets, pills, powders, liquid solutions or suspensions, liposome preparations, injectable and infusible solutions. The preferred form depends on the intended mode of administration and therapeutic application. Typically, a sterile solution of a salen-metal complex in an aqueous solvent (e.g., saline) will be administered intravenously. The compositions also preferably include conventional pharmaceutically acceptable carriers and adjuvants which are known to those of skill in the art. See, e.g., *Remington's Pharmaceutical Sciences*, Mack Publishing Co.: Easton, Pa., 17th Ed. (1985). Generally, administration will be by oral or parenteral (including subcutaneous, intramuscular, intravenous, and intradermal) routes, or by topical application or infusion into a body cavity, or as a bathing solution for tissues during surgery.

It should, of course, be understood that the methods of this invention can be used in combination with other antioxidant agents that have SOD activity, catalase activity, GSH-Px activity, or are free radical scavengers or inhibitors of free radical formation. While it is possible to administer the active ingredient of this invention alone, it is believed preferable to present it as part of a pharmaceutical formulation. The formulations of the present invention comprise at least one compound of this invention in a therapeutically or pharmaceutically effective dose together with one or more pharmaceutically or therapeutically acceptable carriers and optionally other therapeutic ingredients. Various considerations are described, e.g., in Gilman et al. (eds) (1990) *Goodman and Gilman's: The Pharmacological Bases of Therapeutics,* 8th Ed., Pergamon Press; and *Remington's* supra, each of which is hereby incorporated herein by reference. Methods for administration are discussed therein, e.g., for oral, intravenous, intraperitoneal, or intramuscular administration, and others. Pharmaceutically acceptable carriers will include water, saline, buffers, and other compounds described, e.g., in the Merck Index, Merck & Co., Rahway, N.J. incorporated herein by reference.

The pharmaceutical compositions will be administered by parenteral or oral administration for prophylactic and/or therapeutic treatment. The pharmaceutical compositions can be administered in a variety of unit dosage forms depending upon the method of administration. For example, unit dosage forms suitable for oral administration include powder, tablets, pills, capsules, and dragees.

The pharmaceutical compositions will often be administered intravenously. Thus, this invention provides compositions for intravenous administration which comprise a solution of the compound dissolved or suspended in an acceptable carrier, preferably an aqueous carrier. A variety of aqueous carriers can be used, e.g., water, buffered water, 0.4% saline, and the like. Often, the antioxidant salen-metal complex(es), such as C7 or C12, may be dissolved in an organic solvent (e.g., dimethylsulfoxide) and either applied directly or diluted into an aqueous solvent. Typically, antioxidant salen-metal complexes that are relatively lipophilic (e.g., C9, C12) are dissolved in an organic solvent such as DMSO and, if desired, subsequently diluted into a more polar solvent, such as water. These compositions will sometimes be sterilized by conventional, well known sterilization techniques, or can preferably be sterile filtered. The resulting aqueous solutions can be packaged for use as is, or lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, triethanolamine oleate, and the like.

For solid compositions, conventional nontoxic solid carriers can be used which include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 0.001–95% of active ingredient, preferably about 20%.

The compositions containing the compounds can be administered for prophylactic and/or therapeutic treatments. In therapeutic applications, compositions are administered to a patient already suffering from a disease, as described above, in an amount sufficient to cure or at least partially arrest the symptoms of the disease and its complications. An amount adequate to accomplish this is defined as "therapeutically effective amount or dose." Amounts effective for this use will depend on the severity of the disease and the weight and general state of the patient.

In prophylactic applications, compositions containing the compounds of the invention are administered to a patient susceptible to or otherwise at risk of a particular disease. Such an amount is defined to be a "prophylactically effective amount or dose." In this use, the precise amounts again depend on the patient's state of health and weight.

For solid compositions, conventional non-toxic solid excipients include, for example, pharmaceutical grades of mannitol, lactose, starch, magnesium stearate, talcum, celluloses, glucose, sucrose, magnesium carbonate, and the like may be used. The active compound as defined above may be formulated as suppositories using, for example, triglycerides, for example, the Witepsols, as the carrier. Liquid pharmaceutically administerable compositions can, for example, be prepared by dissolving, dispersing, etc. an active compound as defined above and optional pharmaceutical adjuvants in a excipient, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences*, Mack Publishing Company, Easton, Pa. 17th Edition, 1985. The composition or formulation to be administered will, in any event, contain an effective amount of the active compound(s).

For oral administration, a pharmaceutically acceptable non-toxic composition is formed by the incorporation of any of the normally employed excipients, such as, for example pharmaceutical grades of mannitol, lactose, starch, magnesium stearate, talcum, celluloses, glucose, sucrose, magnesium, carbonate, and the like. Such compositions take the form of solutions, suspensions, tablets, capsules, powders, sustained release formulations and the like. Such compositions may contain 0.01–95% active ingredient, preferably 1–70%.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents and the like, such as for example, sodium acetate, sorbitan monolaurate, triethanolamine oleate, etc.

A more recently devised approach for parenteral administration employs the implantation of a slow-release or sustained-release system, such that a constant level of dosage is maintained. See, e.g., U.S. Pat. No. 3,710,795, which is incorporated herein by reference. Antioxidant salen-metal complexes may be administered by transdermal patch (e.g., iontophoretic transfer) for local or systemic application.

Once detectable improvement of the patient's conditions has occurred, a maintenance dose is administered if necessary. Subsequently, the dosage or the frequency of administration, or both, can be reduced, as a function of the symptoms, to a level at which the improved condition is retained. When the symptoms have been alleviated to the desired level, treatment can cease. Patients can, however, require intermittent treatment on a long-term basis upon any recurrence of the disease symptoms or as a prophylactic measure to prevent disease symptom recurrence.

Antioxidant salen-metal complex(es) can also be added to extravasated blood for transfusion to inhibit oxyradical damage to the blood cells and components during storage; similarly, antioxidant salen-metal complexes can also reduce oxyradical damage to blood cells in vivo.

Antioxidant salen-metal complex(es) can also be added to rinse or storage solutions for organs and tissues, such as for organ transplantation or for surgical rinses. For example, excised organs are often placed in a preservation solution prior to transplant into a recipient. Inclusion of at least one species of antioxidant salen-metal complex in a preservation solution, usually at a concentration of about 0.01 mM to 10 mM, is desirable for reducing damage due to ischemia during storage and reperfusion injury following reimplantation in the recipient. Various solutions described in the art are suitable for the inclusion of a salen-metal complex, including but not limited to those described in U.S. Pat. No. 5,145,771; Beyersdorf (1990) *Chem Abst.* 113: 84849w; U.S. Pat. Nos. 4,879,283; 4,873,230; and 4,798,824, incorporated herein by reference.

Typically the antioxidant salen-metal complex is present in the rinse or storage solution at a concentration of about 10 $\mu$M to about 10 mM, and most usually is present at 1 mM. For example, but not to limit the invention, a suitable rinse solution comprises Ringer's solution (102 mM NaCl, 4 mM KCl, 3 mM $CaCl_2$, 28 mM sodium lactate, pH 7.0) or Ringer's solution with 0.1 mM adenosine, and the antioxidant salen-Mn complex C7 at a final concentration of 1 mM. The rinse solution can further comprise additional antioxidants (e.g., glutathione, allopurinol). Preservation or rinse solutions containing an antioxidant salen-metal complex can be used to provide enhanced storage or irrigation of organs (e.g., kidney, liver, pancreas, lung, fetal neural tissue, heart, vascular grafts, bone, ligament, tendon, skin) which is believed to enhance the viability of the tissue and increase resistance to oxidative damage (e.g., as a consequence of ischemia/reperfusion).

Without wishing to be bound by any particular theory of antioxidant or catalytic oxyradical scavenger action, it is believed that excessive dosages or concentrations of the catalytic salen-metal complex(es) of the invention might actually produce free radicals, such as superoxide, possibly in a manner analogous to the presence of large amounts of circulating free iron. On this basis, it is believed that prolonged administration of excessive doses of salen-metal complexes are preferably avoided for antioxidant therapy. However, it is also believed that administration of excessive doses of a catalytically active salen-metal complex may be used to advantage in generating free radicals, such as superoxide, in local areas (e.g., for acne treatment, skin cancer treatment, papillomas) or in cell cultures or transgenic animals harboring a transgene under the transcriptional control of a ARE. For enhancing free radical (e.g., superoxide) generation, it may be preferable to expose the local site, cell culture, or transgenic animal to a hyberbaric environment and/or an oxygen-enriched atmosphere (e.g., greater than about 21 percent molecular oxygen).

Alternatively, the capacity of the antioxidant salen-metal complexes to catalyze the decomposition of reactive oxygen species can be used to advantage to inhibit or slow damage to biological tissues and cells. For example, benzoyl peroxide is a widely used treatment for acne lesions; excessive or inappropriate application of benzoyl peroxide (e.g., accidental application to the eyes) may be treated by local (or if desired, systemic) administration of an antioxidant salen-metal complex (e.g., C7). Similarly, oxyradical-induced damage to connective tissues (e.g., collagen) attendant to exposure to UV light, cigarette smoking, and senescence may be reduced by administration of an antioxidant salen-metal complex approximately concomitant with the exposure to UV light, cigarette smoking, or other oxyradical-generating process (e.g., cellular senescence).

Chemoprotection and Radioprotection

Antioxidant salen-transition metal complexes, typically antioxidant salen-Mn complexes, such as compound C7, are used to protect cells and tissues from free radical-producing agents, such as ionizing radiation and chemotherapeutic agents (e.g., bleomycin). Preferably, a protective dosage comprising at least about 1 µg of salen-Mn complex/kg bodyweight is administered by one or more of several routes (e.g., oral, intraveneous, intraperitoneal, intragastric lavage, enema, portal vein infusion, topical, or inhalation of mist), preferably by injection of liposomes or immunoliposomes for targeted delivery of the antioxidant salen-Mn complexes to protect normal cells, for example, against free radical toxicity associated with chemotherapy or radiotherapy of a neoplasm. The antioxidant salen-transition metal complexes are preferably preadministered to the patient prior to the commencement of the chemotherapy and/or radiotherapy, usually within about 24 hours of commencement, and preferably within about 3-6 hours of commencement of the chemotherapy and/or radiotherapy. Antioxidant salen-Mn may be continually administered to the patient during the course of therapy.

For example, a solution of an antioxidant salen-metal complex can be encapsulated in micelles to form immunoliposomes (U.S. Pat. Nos. 5,043,164, 4,957,735, 4,925,661; Connor and Huang (1985) *J. Cell Biol.* 101: 582; Lasic D. D. (1992) *Nature* 355: 279; *Novel Drug Delivery* (eds. Prescott L. F. and Nimmo W. S.: Wiley, N.Y., 1989); Reddy et al. (1992) *J. Immunol.* 148: 1585; incorporated herein by reference). The immunoliposomes containing the antioxidant salen-metal species will comprise a targeting moiety (e.g., monoclonal antibody) that targets the immunoliposomes to non-neoplastic cells that are otherwise sensitive to radiotherapy or chemotherapy. For example, immunoliposomes having a monoclonal antibody that binds specifically to a hematopoietic stem cell antigen not present on the cancer cells of the individual may be used to target antioxidant salen-metal complexes to hematopoietic stem cells and thereby protect said stem cells against radiotherapy or chemotherapy used to treat the cancer. Such a strategy is preferably employed when the chemotherapeutic agent forms free radicals in vivo (e.g., bleomycin).

Antioxidant salen-Mn complexes are also administered to individuals to prevent radiation injury or chemical injury by free radical generating agents. Military personnel and persons working in the nuclear, nuclear medicine, and/or chemical industries may be administered salen-Mn complexes prophylactically. Antioxidant salen-metal complexes may also be used as chemoprotective agents to prevent chemical carcinogenesis; particularly by carcinogens which form reactive epoxide intermediates (e.g., benzo-[a]-pyrene, benzanthracene) and by carcinogens or promoting agents which form free radicals directly or indirectly (e.g., phenobarbital, TPA, benzoyl peroxide, peroxisome proliferators: ciprofibrate, clofibrate). Persons exposed to such chemical carcinogens are pretreated with an antioxidant salen-metal complex to reduce the incidence or risk of developing neoplasia.

Antioxidant salen-metal complexes can also be formulated into a lipophilic base (or, if desired, an aqueous carrier) for topical application in cosmetics or sunburn-prevention creams and lotions. A typical cosmetic or sunburn-prevention cream or lotion will comprise about between 1 mg to 50 mg of antioxidant salen-metal complex per gram of cosmetic or sunburn-prevention cream or lotion.

Antioxidant salen-metal complexes may also be administered to deep-divers or individuals exposed to hyberbaric environments were oxygen toxicity presents a health risk. Administration of an efficacious dose of an antioxidant salen-metal complex to an individual may permit the breathing or hyberbaric and/or oxygen-enriched gases with a reduced risk of oxygen toxicity. It is also believed that administration of an efficacious dosage of an antioxidant salen-metal complex can reduced toxicity and biological damage associated with exposure to ozone. Prophylactic administration of an antioxidant salen-metal complex to humans who are or will be exposed to ozone is expected to confer an enhanced resistance to ozone toxicity, such as the ozone-induced lung damage noted in geographical areas with high ozone levels (e.g., Los Angeles).

Utility, Testing and Administration

The compounds of the invention, antioxidant salen-transition metal complexes, preferably salen-Mn complexes, are useful treatments for protection against ischemic damage in cardiac and non-cardiac states including myocardial infarction, congestive heart failure, angina, arrhythmia, circulatory disorders, and stroke. The compounds of the invention inhibit the deleterious effects of ischaemia (coronary infarction and reperfusion in the heart; transient myocardial or CNS ischemia during surgery) without direct depressant effects on myocardial contractility. Thus, the compounds are effective in animal models for cardiovascular and CNS diseases, and will be useful for the treatment of myocardial infarction, stroke, brain injury, and transplant surgery, particularly with reperfusion of infarcted areas, arrhythmias, variant and exercise-induced angina, congestive heart failure, stroke and other circulatory disorders, in mammals, particularly in human beings. The salen-Mn complexes are also included in preservation solutions used to bathe excised organs (e.g., heart, kidney, pancreas, liver, lung) during transport and storage of the excised organ prior to transplantion surgery, including skin grafting and corneal grafting. The preservation solutions will typically comprise at least about 1 $\mu$M of an antioxidant salen-metal complex, preferably at least about 1 mM of an antioxidant salen-metal complex.

Administration of the active compound and salts described herein can be via any of the accepted modes of administration for therapeutic agents. These methods include oral, parenteral, transdermal, subcutaneous and other systemic modes. The preferred method of administration is oral, except in those cases where the subject is unable to ingest, by himself, any medication. In those instances it may be necessary to administer the composition parenterally. If the composition comprises an antioxidant salen-metal species having an amino substituent that can be protonated at physiological pH, it is usually preferred that the antioxidant salen-metal complex is dissolved or suspended in a solution having a pH at which the amino substituent is protonated.

The amount of active compound administered will, of course, be dependent on the subject being treated, the subject's weight, the severity of the affliction, the manner of administration and the judgment of the prescribing physician. However, an effective dosage is in the range of 0.01–50 mg/kg/day, preferably 0.5–25 mg/kg/day. For an average 70 kg human, this would amount to 0.7–3500 mg per day, or preferably about 35–1750 mg/day.

Since all of the effects of the salen-Mn compounds herein are achieved through a similar mechanism, dosages (and forms of administration) are within the same general and preferred ranges for all these utilities.

The following examples are offered by way of illustration, not by way of limitation.

EXPERIMENTAL EXAMPLES

In Vitro Catalytic Activities

The antioxidant catalytic activities of the C1, C4, C6, C7, C9, C10, C11, and C12 salen-Mn complexes (see FIG. 3) was determined; superoxide dismutase and catalase activities were determined according to the following method.

Assay

The SOD activity of the compounds was determined by evaluating the inhibition of the reduction of cytochrome C produced by the oxygen free radical generating system, xanthine plus xanthine oxidase. Cytochrome C reduction is monitored spectrophotometrically at 550 nm according to the method described in Darr et al. (1987) *Arch. Biochem. Biophys.* 258: 351, incorporated herein by reference. The concentration of xanthine oxidase is adjusted such that it produces a rate of reduction of cytochrome C at 550 nm of 0.025 absorbance unit per minute. Under these conditions, the amount of SOD activity required to inhibit the rate of cytochrome C reduction by 50 percent (i.e., to a rate of 0.0125 absorbance unit per minute) is defined as one unit of activity. Salen-metal complexes are identified as antioxidants if they have at least 0.1 unit of activity at a concentration of 1 mM under these standard assay conditions.

Catalase activity was measured using a spectrophotometric method in which the decomposition of hydrogen peroxide is monitored at 240 nm according to the method of Aebi et al. (1984) *Methods Enzymol.* 105: 121, incorporated herein by reference. One unit of catalase activity is defined as the amount of enzyme (or salen-metal complex) required to decompose 1 $\mu$mole of hydrogen peroxide in one minute.

Each of the compounds was formulated in saline and was stable with no loss of activity observed after several weeks of storage at room temperature. Frequently, it is desirable to first dissolve the salen-metal complex in an organic solvent (e.g., DMSO) and then dilute the solution into a more polar solvent such as water. This is particularly preferred for salen-metal species that are relatively hydrophobic (e.g., C12).

Table I shows the in vitro SOD and catalase activities of the various salen-Mn complexes tested. SOD and catalase activities are expressed as units/mM.

TABLE I

| Salen-Mn Complex | SOD Activity | Catalase Activity |
|---|---|---|
| C1 | 308 | 262 |
| C4 | 312 | 200 |
| C6 | 812 | 0 |
| C7 | 575 | 200 |
| C9 | 111 | 20 |
| C10 | 69 | 179 |
| C11 | 101 | 46 |
| C12 | 4397 | 144 |

In Vivo Biological Activities

A widely used assay to determine the therapeutic potential of molecules in brain ischemia (stroke) consists of evaluating their ability to prevent irreversible damage induced by an anoxic episode in brain slices maintained under physiological conditions. Rat brain slices were maintained at 35° C. in an interface chamber in an artificial cerebrospinal fluid containing: 124 mM NaCl 3 mM KCl, 1.25 mM $KH_2PO_4$, 3 mM CaCl, 1, mM $MgCl_2$, 26 mM $NaHCO_3$, 10 mM D-glucose, and 2 mM L-ascorbate, continuously gassed with a mixture of $O_2:CO_2$ (95:5). The atmosphere of the chamber was also continuously gased with the mixture of $O_2:CO_2$ (95:5), except during the anoxic episode when it was replaced by $N_2$. Axons were electrically stimulated and the evoked excitatory post-synaptic potentials (EPSPs) were recorded using microelectrodes.

Figure 4:
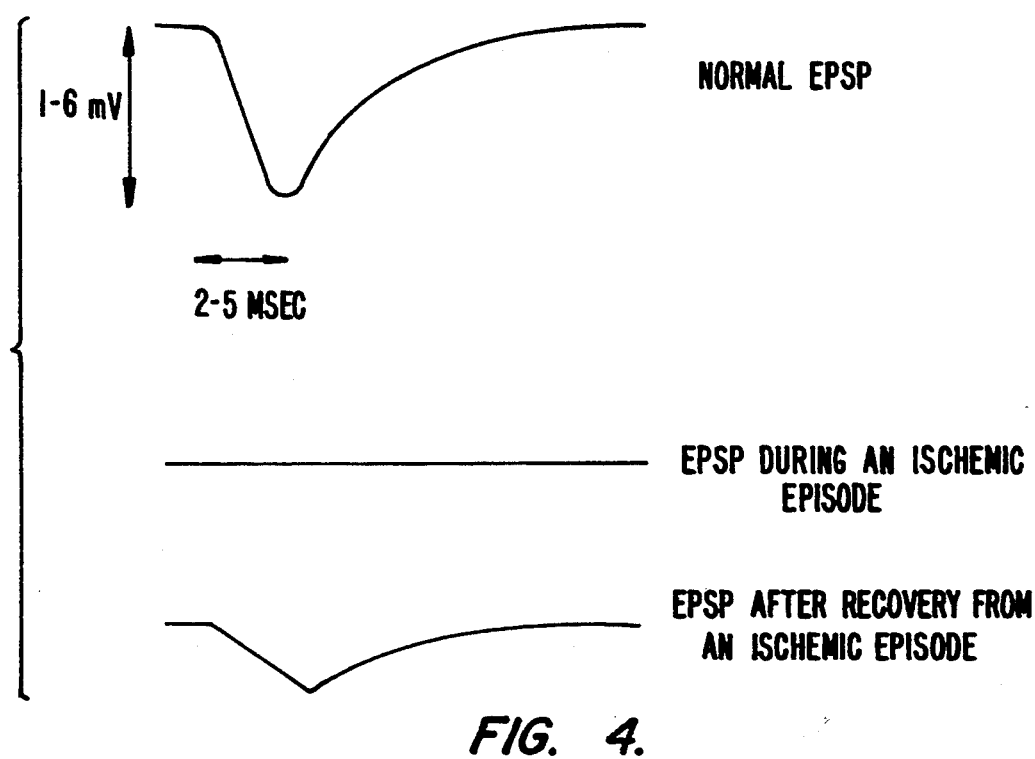
FIG. 4 shows schematically the effect of an ischemic/reoxygenation episode on synaptic transmission in isolated brain slices.

FIG. 4 shows the schematic of an EPSP recorded under normal conditions (A), five minutes following replacement of $O_2$ with $N_2$ (ischemic episode, B), and 30 to 40 minutes following reoxygenation (C). The extent of permanent damage can be quantified by measuring both the amplitude (in mV) and the initial slope (in mV/msec) of the EPSP.

Figure 5:
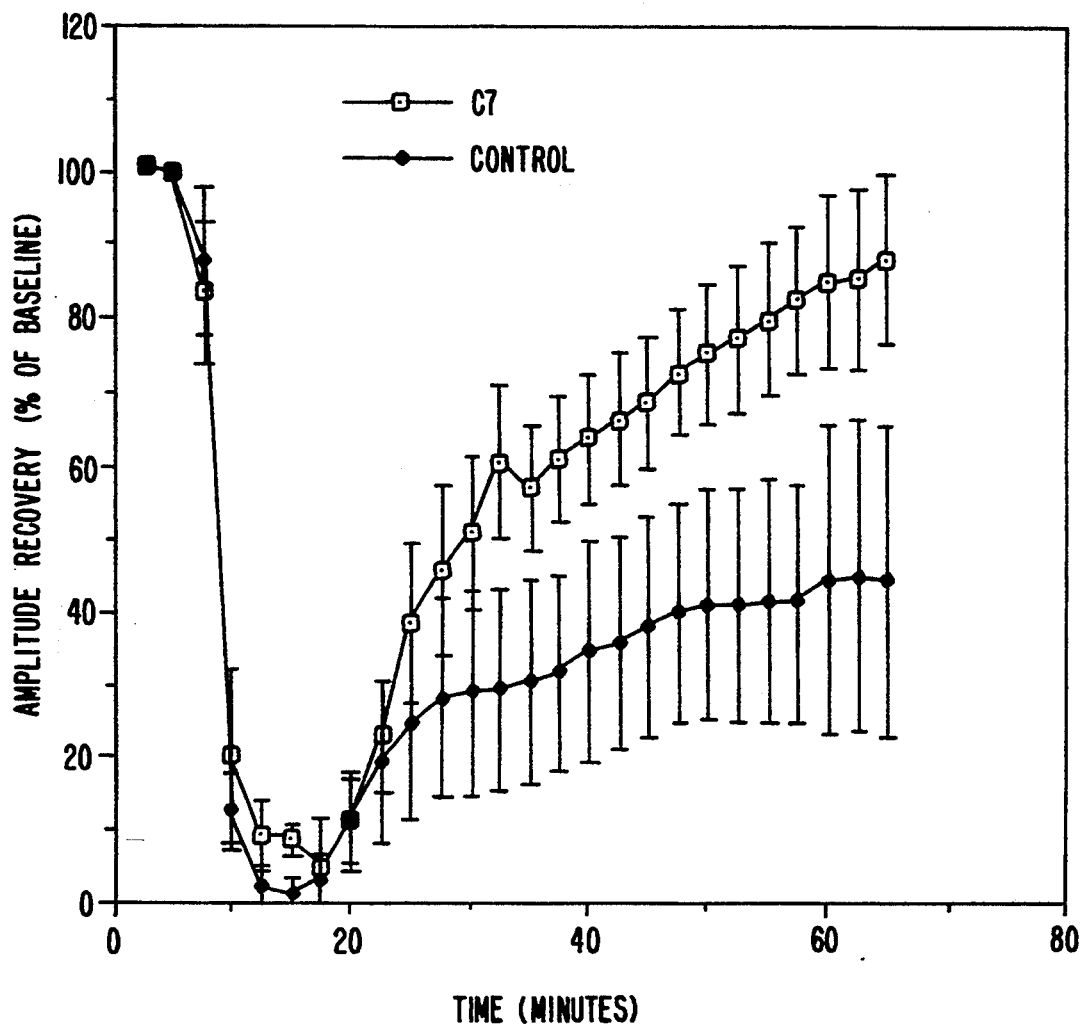
FIG. 5 shows the effect of a salen-Mn complex on EPSP amplitude following an episode of ischemia/reoxygenation.
Figure 6:
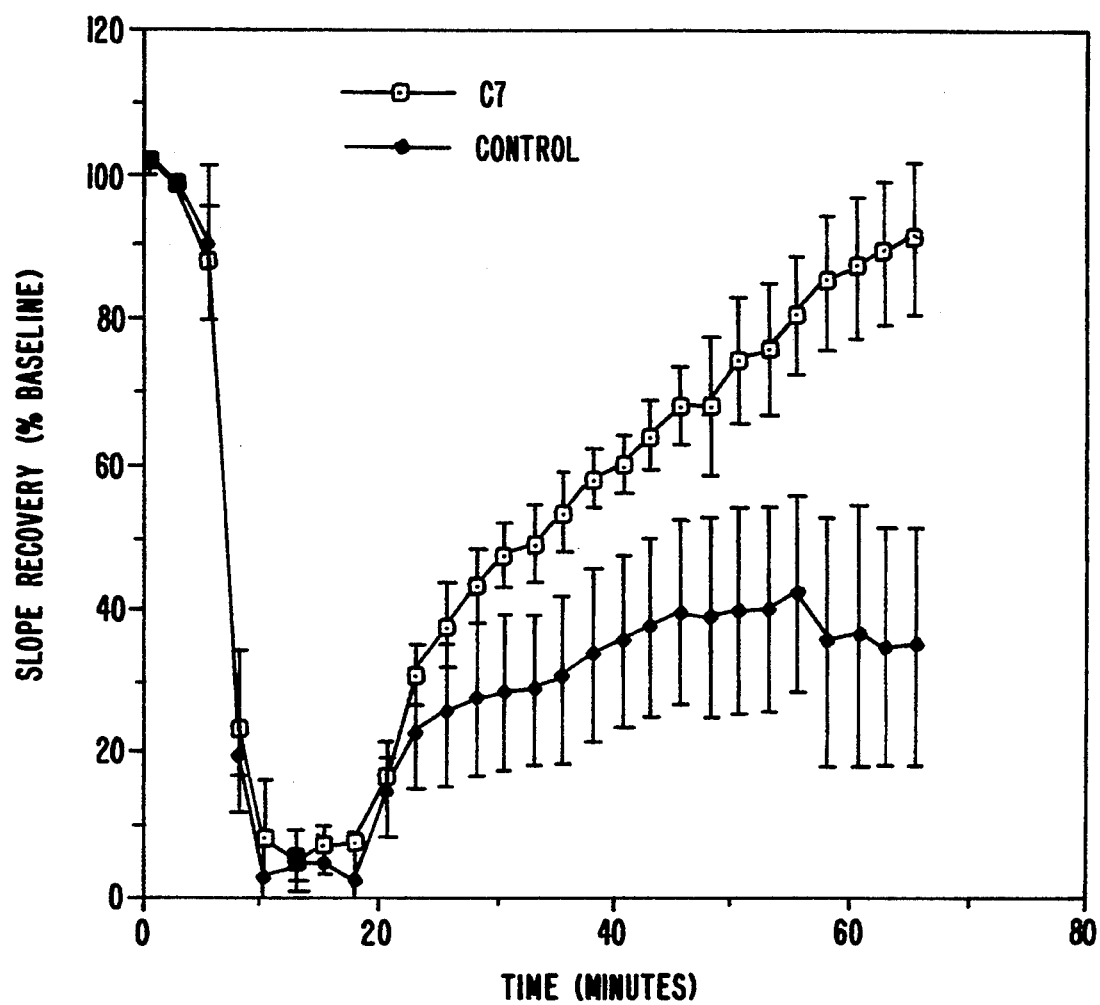
FIG. 6 shows the effect of a salen-Mn complex on EPSP initial slope following an episode of ischemia/reoxygenation.

FIGS. 5 and 6 show the protective effect of the antioxidant salen-Mn complex designated C7 in the rat brain slice ischemia EPSP system. Brain slices were incubated in the absence or presence of 50 $\mu$M C7 and subjected to an episode of ischemia/reoxygenation. After 5 minutes of baseline recording, $O_2$ was replaced by $N_2$ for an average of 5 minutes. $O_2$ was then reintroduced and recording was continued for another 50 minutes. Samples with 50 $\mu$M C7 showed that both the amplitude and slopes of the EPSPs recovered to pre-ischemia levels. In contrast, recovery in untreated brain slices was only about 40% of pre-ischemia levels.

Figure 7:
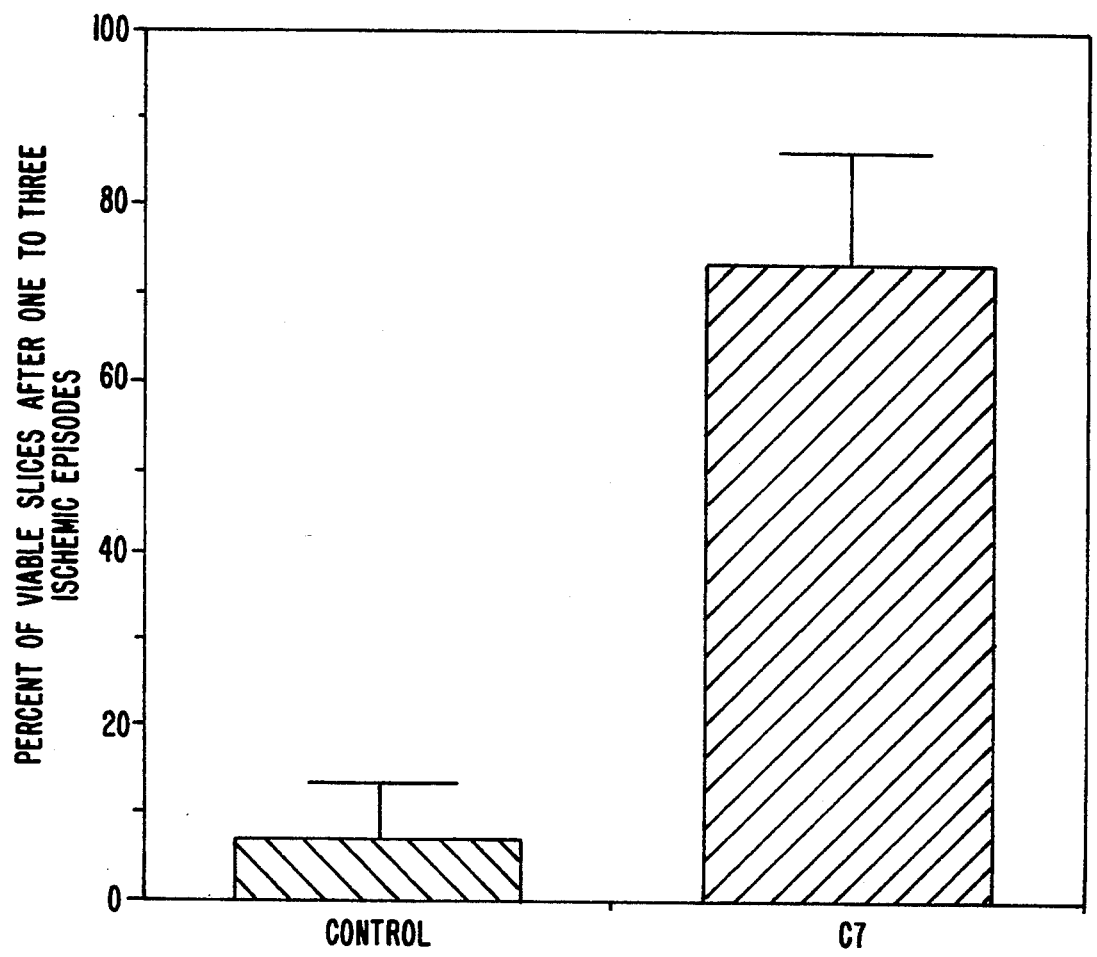
FIG. 7 shows the effect of a salen-Mn complex on brain slice viability following repeated episodes of ischemia/reoxygenation.

As an additional assessment of efficacy, the percentage of viable slices following repeated ischemic episodes was evaluated. FIG. 7 demonstrates that, while without any treatment this percentage is very low (6%), it was as high as 70% in slices treated with 50 μM C7. A slice was considered viable if an EPSP of 3 mV amplitude could be elicited by increasing stimulation intensity.

Animal Model Testing

An animal model of Parkinson's disease involving iatrogenic hydroxyl radical generation by MPTP (Chiueh et al. (1992) Synapse 11: 346, incorporated herein by reference) was used to evaluate the protective effect of C7 on free radical-induced damage. The neurotoxin, MPTP, has been shown to lead to the degeneration of dopaminergic neurons in the brain, thus providing a good model of experimentally induced Parkinson's disease (e.g., iatrogenic toxicity). This model is now widely accepted in the art and is used for evaluating potential therapeutic agents for this disease.

Figure 8A:
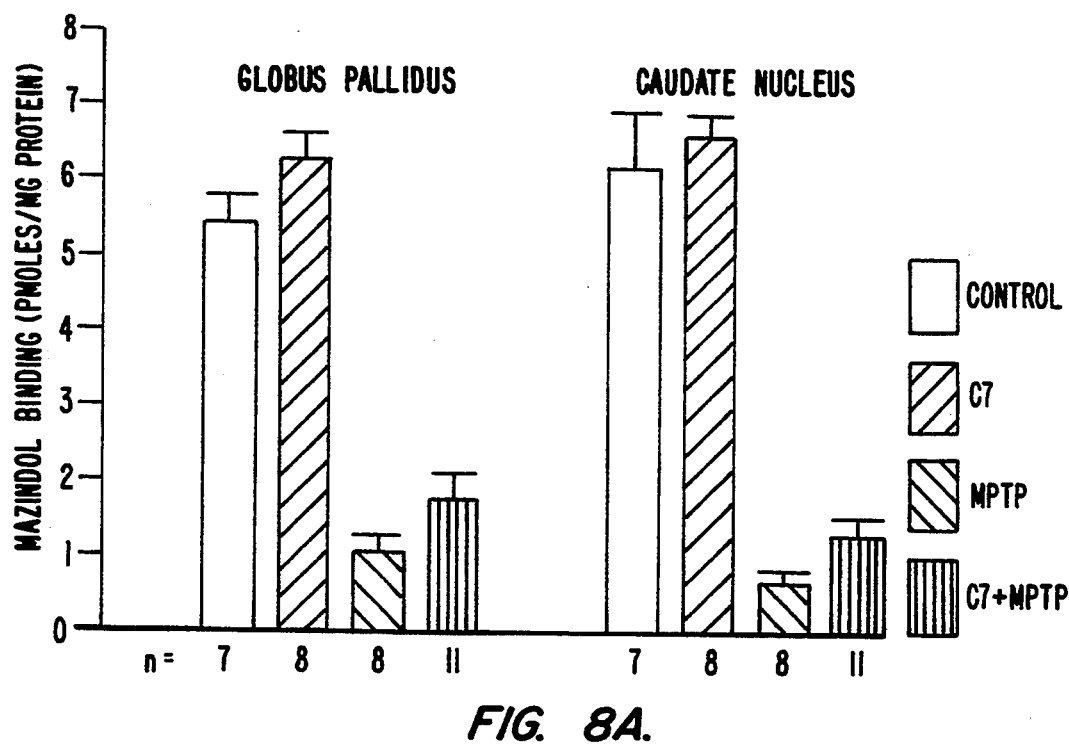
FIG. 8 shows the protective effect of a salen-Mn complex in an animals model of iatrogenic Parkinson's disease.
Figure 8B:
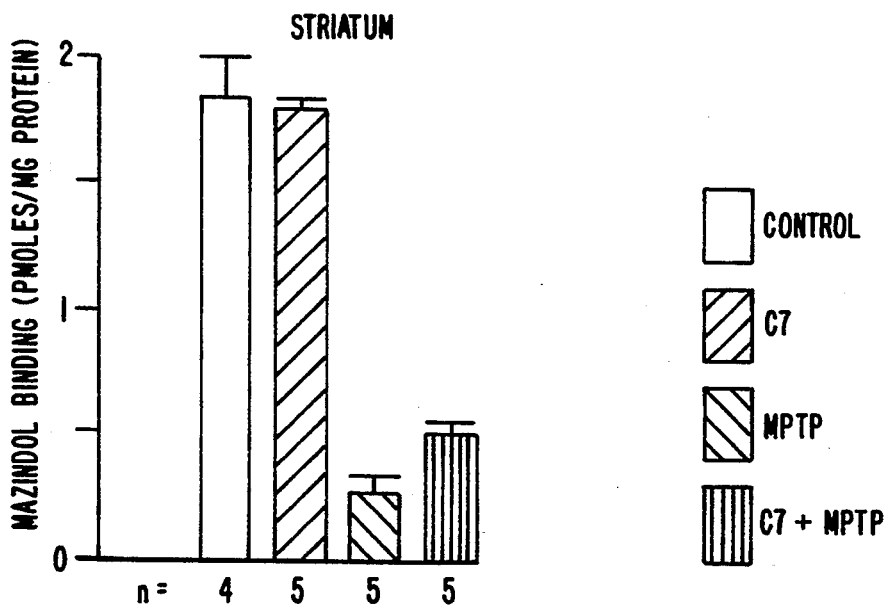

The number of dopaminergic neurons in brains of mice treated with either: (1) MPTP alone, (2) the antioxidant salen-metal complex C7 alone, (3) pretreatment with C7 and then MPTP, or (4) untreated controls, were assayed by measurement of the binding of the dopamine reuptake ligand, mazindol. Tritiated mazindol was used for binding studies on samples of the globus pallidus, caudate nucleus, and striatum of mouse brain according to conventional methods; specific binding of tritiated mazindol was determined autoradiographically or by membrane binding (specific binding to the membrane fraction). The experiment was performed over a 7 day period. Mice in the MPTP group were treated intraperitoneally with MPTP alone (40 mg/kg each day on days 1 and 2). Mice in the MPTP+C7 group were pretreated with C7 (33 mg/kg, i.p.) immediately prior to MPTP on days 1 and 2, and were given C7 (33 mg/kg) alone on day 3. The animals were sacrificed after 7 days. The results shown in FIG. 8 show a significant protective effect conferred in vivo by the salen-Mn complex, C7. FIG. 8 shows that the number of dopaminergic neurons present in various regions of the mouse brain were not adversely affected by the antioxidant salen-metal complex C7; but dopaminergic neurons were reduced to about 15 percent of control values in mice treated with MPTP alone; however pretreatment with C7 approximately doubled the number of surviving dopaminergic neurons present in mice subsequently treated with MPTP. Lack of toxicity of C7 was shown by the absence of adverse health effects in the C7-treated animals over the 7 day test period.

These data demonstrate that the salen-Mn complexes display therapeutic efficacy in vivo in rodent models of human disease and also indicate that the salen-Mn complexes cross the blood-brain barrier efficiently. Taken together, these data indicate a dramatic efficacy of salen-Mn complexes to prevent free radical-induced damage and ischemia/reoxygenation injury in the brain.

The foregoing description of the preferred embodiments of the present invention has been presented for purposes of illustration and description. They are not intended to be exhaustive or to limit the invention to the precise form disclosed, and many modifications and variations are possible in light of the above teaching.

Such modifications and variations which may be apparent to a person skilled in the art are intended to be within the scope of this invention.

We claim:

1. A pharmaceutical composition comprising a therapeutically effective dose of an antioxidant salen-metal complex in a pharmaceutically acceptable form, wherein the antioxidant salen-metal complex has the structural formula

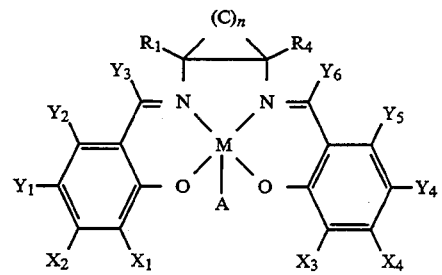

wherein M is manganese;

A is H or halogen;

n is 0, 4, 5, or 6, wherein $C_n$ is absent if n=0 and is a saturated hydrocarbon chain if n=4, 5, or 6;

$R_1$ and $R_4$ are independently selected from the group consisting of H, phenyl, lower alkoxy, and lower fatty acid esters;

$X_1$ and $X_3$ are independently selected from the group consisting of H, lower alkyl, amine, lower alkylamino, and halogen;

$X_2$ and $X_4$ are H;

$Y_1$ and $Y_4$ are independently selected from the group consisting of H, lower alkyl, halogen, and lower alkoxy;

$Y_2$, $Y_3$, $Y_5$ and $Y_6$ are H; and all remaining substituent positions are H.

2. A pharmaceutical composition according to claim 1 wherein the antioxidant salen-metal complex is selected from the group consisting of:

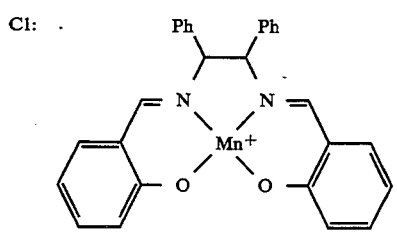

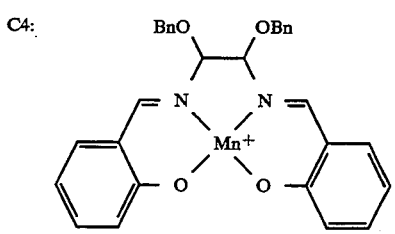

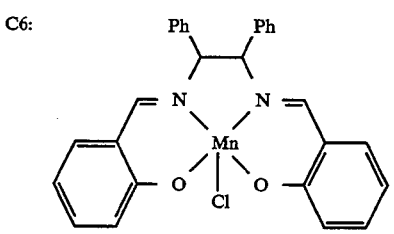

C7: 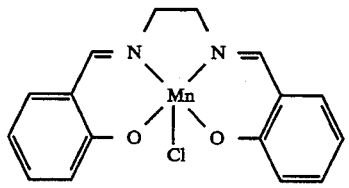
and
C9: 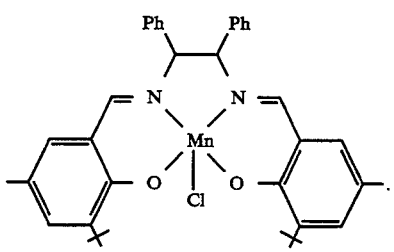
3. A pharmaceutical composition comprising a therapeutically effective dose of an antioxidant salen-metal complex in a pharmaceutically acceptable form, wherein the antioxidant salen-metal complex is selected from the group consisting of:
C1: 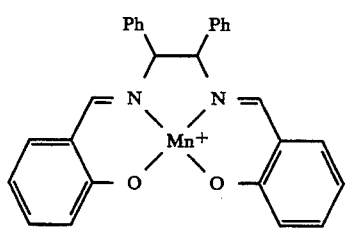
C4: 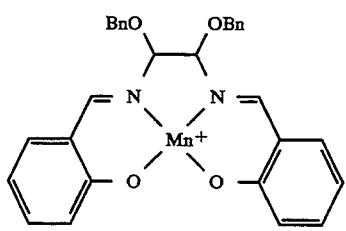
C6: 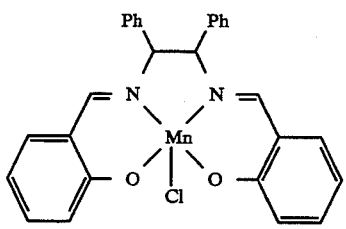
C7: 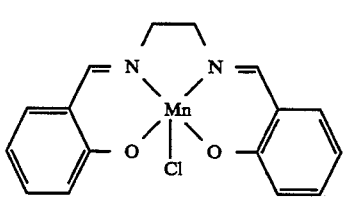
C9: 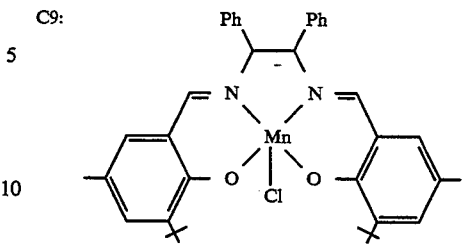
C15: 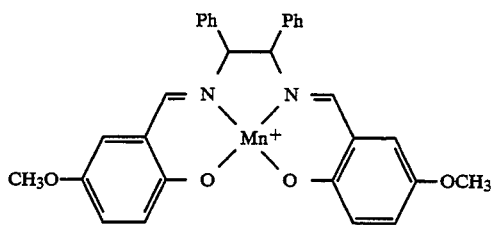
C17: 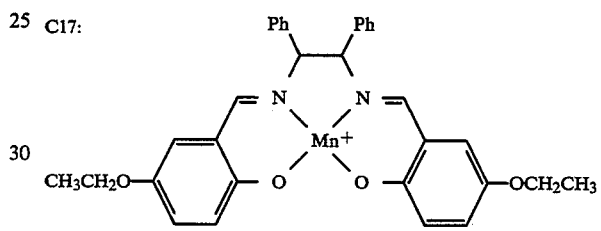
C20: 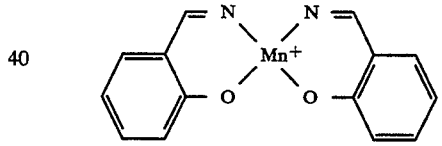
C22: 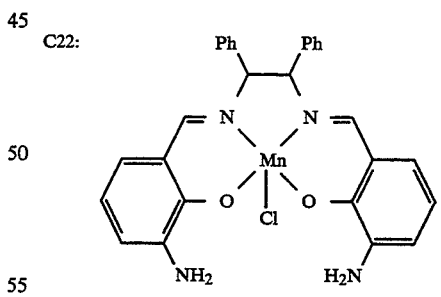
C23: 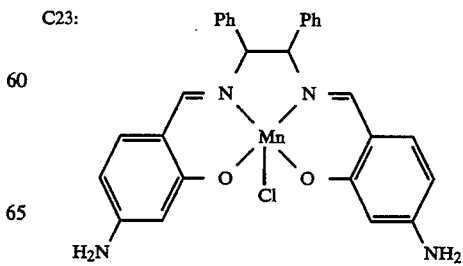

C25:
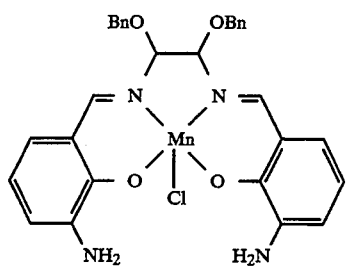

C27:
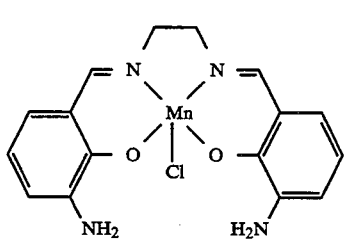

and

C28:
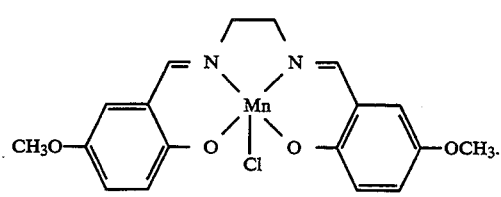

4. A pharmaceutical composition comprising a therapeutically effective dose of an antioxidant salen-metal complex in a pharmaceutically acceptable form, wherein the antioxidant salen-metal complex is selected from the group consisting of:

C10:
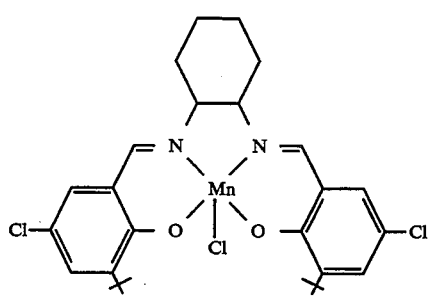

C11:

C12:

and

C29:

5. A pharmaceutical composition according to claim 3, wherein the antioxidant salen-metal complex is the SOD-mimetic C7:
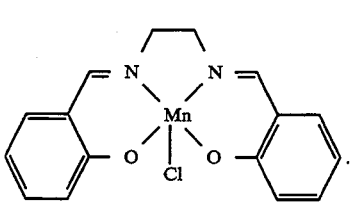

6. A pharmaceutical composition according to claim 5, wherein the pharmaceutical composition comprises at least 10 mg of C7:
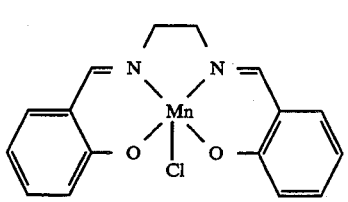

in a form suitable for parenteral administration.

* * * * *